US011730861B2

(12) United States Patent
Spiegel

(10) Patent No.: US 11,730,861 B2
(45) Date of Patent: Aug. 22, 2023

(54) HYDROGEL DEVICES AND METHODS OF MAKING AND USE THEREOF

(71) Applicant: The Methodist Hospital System, Houston, TX (US)

(72) Inventor: Aldona Jedrysiak Spiegel, Houston, TX (US)

(73) Assignee: The Methodist Hospital System, Houston, TX (US)

( * ) Notice: Subject to any disclaimer, the term of this patent is extended or adjusted under 35 U.S.C. 154(b) by 0 days.

(21) Appl. No.: 17/873,553

(22) Filed: Jul. 26, 2022

(65) Prior Publication Data
US 2023/0119855 A1 Apr. 20, 2023

Related U.S. Application Data

(60) Provisional application No. 63/255,565, filed on Oct. 14, 2021.

(51) Int. Cl.
*A61L 27/52* (2006.01)
*A61L 27/38* (2006.01)
*A61L 27/54* (2006.01)
*B33Y 80/00* (2015.01)

(52) U.S. Cl.
CPC ............ *A61L 27/52* (2013.01); *A61L 27/3808* (2013.01); *A61L 27/54* (2013.01); *A61L 2300/64* (2013.01); *A61L 2400/18* (2013.01); *A61L 2430/04* (2013.01); *B33Y 80/00* (2014.12)

(58) Field of Classification Search
None
See application file for complete search history.

(56) References Cited

U.S. PATENT DOCUMENTS

| | | | |
|---|---|---|---|
| 6,344,489 | B1 | 2/2002 | Spears |
| 10,799,336 | B2 | 10/2020 | Hutmacher et al. |
| 2014/0078636 | A1 | 3/2014 | Uchaykin |
| 2019/0343889 | A1 | 11/2019 | Luukko et al. |
| 2020/0339925 | A1 | 10/2020 | Miller et al. |

FOREIGN PATENT DOCUMENTS

| | | |
|---|---|---|
| WO | 2008079997 A2 | 7/2008 |
| WO | 2016154070 A1 | 9/2016 |
| WO | 2018089401 A1 | 5/2018 |
| WO | 20200168327 A1 | 8/2020 |

OTHER PUBLICATIONS

Baranski JD et al. Geometric control of vascular networks to enhance engineered tissue integration and function. Proc Natl Acad Sci U S A. 2013. doi:10.1073/pnas.1217796110.

Bayram Y et al. "The use of autologous fat grafts in breast surgery: A literature review," Archives of Plastic Surgery, 2019, 46(6), 498-510.

Cui H et al. "3D Bioprinting for Organ Regeneration," Advanced Healthcare Materials, 2017, 6, 1601118.

Faglin P et al. "Rationale for the design of 3D-printable bioresorbable tissue-engineering chambers to promote the growth of adipose tissue," Scientific Reports, 2020, 10, 11779.

Gabriel A et al. Fat grafting and breast reconstruction: tips for ensuring predictability. Gland Surg. 2015. doi:10.3978/j.issn.2227-684X.2015.04.18.

Grigoryan B et al. "Multivascular networks and functional intravascular topologies within biocompatible hydrogels," Science, 2019, 364, 458-464.

Hao W et al. "3D printing-based drug-loaded implanted prosthesis to prevent breast cancer recurrence post-conserving surgery," Asian Journal of Pharmaceutical Sciences, 2021, 16(1), 86-96.

Ho Quoc C et al. Breast reconstruction with fat grafting and BRAVA® pre-expansion: Efficacy evaluation in 45 cases. Ann Chir Plast Esthet. 2016. doi:10.1016/j.anplas.2015.06.010.

Jafarkhani M et al. "Bioprinting in Vascularization Strategies," Iranian Biomedical Journal, 2019, 23(1), 9-20.

Khouri RK et al. Tissue-engineered breast reconstruction with brava-assisted fat grafting: A 7-year, 488-patient, multicenter experience. Plast Reconstr Surg. 2015. doi:10.1097/PRS.0000000000001039.

Ng WL et al. "Print Me An Organ! Why We Are Not There Yet," Progress in Polymer Science, 2019, 97, 01145.

Sarker MD et al. "3D biofabrication of vascular networks for tissue regeneration: A report on recent advances," Journal of Pharmaceutical Analysis, 2018, 8, 277-296.

Szklanny AA et al. "3D Bioprinting of Engineered Tissue Flaps with Hierarchical Vessel Networks (VesselNet) for Direct Host-To-Implant Perfusion ," Advanced Materials, 2021, 33, 2102661.

Uroskie TW et al. History of Breast Reconstruction. Semin Plast Surg. 2004. doi:10.1055/s-2004-829040.

Zhang B et al. Biodegradable scaffold with built-in vasculature for organ-on-a-chip engineering and direct surgical anastomosis. Nat Mater. 2016. doi:10.1038/nmat4570.

(Continued)

*Primary Examiner* — Robert A Wax
*Assistant Examiner* — Randeep Singh
(74) *Attorney, Agent, or Firm* — Meunier Carlin & Curfman LLC

(57) ABSTRACT

Disclosed herein are hydrogel devices and methods of making an use thereof. The devices can comprise: a continuous hydrogel matrix; a first chamber in the hydrogel matrix; and a second chamber in the hydrogel matrix; wherein the first chamber and the second chamber are each independently perfusable; wherein the first chamber is fluidly independent from the second chamber; wherein the first chamber is configured to be at least partially filled with adipose tissue; wherein the second chamber is configured to be at least partially filled with an oxygenated fluid; wherein the first chamber is defined by a first border; wherein the second chamber is defined by a second border; and wherein the first chamber and the second chamber are spaced apart from each other by an average distance of from 50 micrometers (microns, µm) to 800 µm as measured from the first border to the second border.

30 Claims, 10 Drawing Sheets

(56) References Cited

OTHER PUBLICATIONS

International Search Report and Written Opinion dated Feb. 2, 2023 in connection with related International Application No. PCT/US22/46662 (8 pages).

HYDROGEL DEVICES AND METHODS OF MAKING AND USE THEREOF

CROSS-REFERENCE TO RELATED APPLICATIONS

This application claims the benefit of priority to U.S. Provisional Application No. 63/255,565 filed Oct. 14, 2021, which is hereby incorporated herein by reference in its entirety.

BACKGROUND

Breast cancer is a multifaceted disease. The treatment of which goes far beyond the initial declaration of "Cancer-Free." Many breast cancer patients have a mastectomy or lumpectomy as part of their cancer treatment. These women often experience significant anxiety and depression regarding their mastectomy or lumpectomy. Breast reconstruction can reduce anxiety and depression in these patients. Reconstruction, as it stands, is an imperfect science. With current technologies and techniques needing improvement, new methods of reconstruction are necessary. The devices and methods discussed herein address these and other needs.

SUMMARY

In accordance with the purposes of the disclosed devices and methods as embodied and broadly described herein, the disclosed subject matter relates to hydrogel devices and methods of making and use thereof.

For example, disclosed herein are devices comprising: a continuous hydrogel matrix; a first chamber in the hydrogel matrix; and a second chamber in the hydrogel matrix; wherein the first chamber and the second chamber are each independently perfusable; wherein the first chamber is fluidly independent from the second chamber; wherein the first chamber is configured to be at least partially filled with adipose tissue; wherein the second chamber is configured to be at least partially filled with an oxygenated fluid; wherein the first chamber is defined by a first border; wherein the second chamber is defined by a second border; and wherein the first chamber and the second chamber are spaced apart from each other by an average distance of from 50 micrometers (microns, $\mu m$) to 800 $\mu m$ as measured from the first border to the second border.

In some examples, the first chamber and the second chamber are entangled.

In some examples, the first chamber and the second chamber are spaced apart from each other by an average distance of from 200 $\mu m$ to 400 $\mu m$. In some examples, the first chamber and the second chamber are spaced apart from each other by an average distance of from 250 $\mu m$ to 350 $\mu m$.

In some examples, the first chamber has an average characteristic dimension of from 150 $\mu m$ to 10 millimeters (mm). In some examples, the first chamber has an average characteristic dimension of from 300 $\mu m$ to 1 mm.

In some examples, the first chamber further comprises an inlet configured to receive the adipose tissue.

In some examples, the second chamber has an average characteristic dimension of from 5 $\mu m$ to 500 $\mu m$.

In some examples, the second chamber has a longitudinal axis, an inlet, and an outlet axially spaced apart from the inlet, wherein the inlet is configured to receive the oxygenated fluid and the outlet is configured to discharge the oxygenated fluid. In some examples, the oxygenated fluid comprises blood and the inlet and the outlet of the second chamber are each independently configured to be connected to a blood vessel.

In some examples, the second chamber is lined with a plurality of cells. In some examples, the plurality of cells comprise endothelial cells.

In some examples, the device further comprises a third chamber in the hydrogel matrix, wherein the third chamber is perfusable and fluidly independent from the first chamber and the second chamber.

In some examples, the third chamber has an average characteristic dimension of from 1.5 $\mu m$ to 250 $\mu m$.

In some examples, the third chamber is entangled with the first chamber and/or the second chamber.

In some examples, the third chamber is configured to be at least partially filled with a lymphatic fluid.

In some examples, the third chamber further comprises a port configured to allow for the flow of the lymphatic fluid into and out of the third chamber.

In some examples, the third chamber has a longitudinal axis, an inlet, and an outlet axially spaced apart from the inlet, wherein the inlet is configured to receive the lymphatic fluid and the outlet is configured to discharge the lymphatic fluid.

In some examples, the inlet and the outlet of the third chamber are each independently configured to be connected to a lymphatic vessel.

In some examples, the first chamber, the second chamber, and the third chamber (when present) are each independently formed from a model based on a tessellation of polyhedrons.

In some examples, the first chamber, the second chamber, and the third chamber (when present) are each independently formed from a computational 3D space-filling model. In some examples, the computational 3D space-filling model is a fractal space-filling model.

In some examples, the device further comprises a therapeutic agent dispersed within the hydrogel matrix. In some examples, the therapeutic agent is dispersed substantially homogeneously throughout the hydrogel matrix. In some examples, the therapeutic agent comprises an anticancer agent, anti-inflammatory agent, antimicrobial agent, or a combination thereof. In some examples, the therapeutic agent comprises a chemotherapeutic agent, an immunotherapeutic agent, or a combination thereof.

In some examples, the first chamber is at least partially filled with adipose tissue.

In some examples, the device is implantable in a subject.

In some examples, the device is anatomically designed for the subject.

In some examples, the adipose tissue comprises autologous adipose tissue.

In some examples, the second chamber is configured to be connected to a blood vessel of the subject; the third chamber, when present, is configured to be connected to a lymphatic vessel the subject; or a combination thereof.

In some examples, the hydrogel matrix is configured to be stable for an amount of time of from 6 weeks to 12 weeks after the device is implanted in the subject.

In some examples, the hydrogel is monolithic.

In some examples, the hydrogel matrix is porous.

In some examples, the hydrogel matrix is biocompatible.

In some examples, the hydrogel matrix is biodegradable.

In some examples, the hydrogel matrix comprises a photopolymerized polymer network derived from a photosensitive polymer.

In some examples, the hydrogel matrix comprises a cross-linked polymer network derived from a photosensitive polymer.

In some examples, the hydrogel matrix comprises a plurality of layers, each layer comprising a cross-linked polymer network derived from a photosensitive polymer. In some examples, the hydrogel matrix comprises from 10 layers to 10,000 layers. In some examples, each layer independently has an average thickness of from 5 micrometers (microns, μm) to 100 μm.

In some examples, the photosensitive polymer comprises poly(ethylene glycol) diacrylate (PEGDA), poly(ethylene glycol) dimethacrylate (PEGDMA), poly(ethylene glycol) diacrylamide (PEGDAAm), gelatin methacrylate (GelMA), collagen methacrylate, silk methacrylate, hyaluronic acid methacrylate, chondroitin sulfate methacrylate, elastin methacrylate, cellulose acrylate, dextran methacrylate, heparin methacrylate, NIPAAm methacrylate, Chitosan methacrylate, polyethylene glycol norbornene, polyethylene glycol dithiol, thiolated gelatin, thiolated chitosan, thiolated silk, PEG based peptide conjugates, cell-adhesive poly(ethylene glycol), MMP-sensitive poly(ethylene glycol), PEGylated fibrinogen, or a combination thereof.

In some examples, the photosensitive polymer comprises poly(ethylene glycol) diacrylate (PEGDA).

In some examples, the photosensitive polymer has a molecular weight of from 2-50 kiloDaltons (kDa).

In some examples, the hydrogel matrix further comprises a photoabsorber. In some examples, the photoabsorber is biocompatible.

In some examples, the device is produced by additive manufacturing.

In some examples, the device is produced by stereolithography.

In some examples, the device is monolithic.

Also disclosed herein are devices comprising multiple joined subunits, wherein each subunit is any of the devices disclosed herein.

Also disclosed herein are devices comprising multiple joined subunits, wherein each subunit independently comprises: a continuous hydrogel matrix; and one or more chambers in the continuous hydrogel matrix; wherein each of the one or more chambers in each subunit is fluidly independent from one another; wherein, when multiple subunits are joined together, the device comprises: a continuous hydrogel matrix; a first chamber in the hydrogel matrix; and a second chamber in the hydrogel matrix; wherein the first chamber and the second chamber are each independently perfusable; wherein the first chamber is fluidly independent from the second chamber; wherein the first chamber is configured to be at least partially filled with adipose tissue; wherein the second chamber is configured to be at least partially filled with an oxygenated fluid; wherein the first chamber is defined by a first border; wherein the second chamber is defined by a second border; and wherein the first chamber and the second chamber are spaced apart from each other by an average distance of from 50 micrometers (microns, μm) to 800 μm as measured from the first border to the second border.

In some examples, the first chamber and the second chamber are entangled.

In some examples, the first chamber and the second chamber are spaced apart from each other by an average distance of from 200 μm to 400 μm. In some examples, the first chamber and the second chamber are spaced apart from each other by an average distance of from 250 μm to 350 μm.

In some examples, the first chamber has an average characteristic dimension of from 150 μm to 10 millimeters (mm). In some examples, the first chamber has an average characteristic dimension of from 300 μm to 1 mm.

In some examples, the first chamber further comprises an inlet configured to receive the adipose tissue.

In some examples, the second chamber has an average characteristic dimension of from 5 μm to 500 μm.

In some examples, the second chamber has a longitudinal axis, an inlet, and an outlet axially spaced apart from the inlet, wherein the inlet is configured to receive the oxygenated fluid and the outlet is configured to discharge the oxygenated fluid.

In some examples, the oxygenated fluid comprises blood and the inlet and the outlet of the second chamber are each independently configured to be connected to a blood vessel.

In some examples, the second chamber is lined with a plurality of cells. In some examples, the plurality of cells comprise endothelial cells.

In some examples, the device further comprises a third chamber in the hydrogel matrix, wherein the third chamber is perfusable and fluidly independent from the first chamber and the second chamber.

In some examples, the third chamber has an average characteristic dimension of from 1.5 μm to 250 μm.

In some examples, the third chamber is entangled with the first chamber and/or the second chamber.

In some examples, the third chamber is configured to be at least partially filled with a lymphatic fluid.

In some examples, the third chamber further comprises a port configured to allow for the flow of the lymphatic fluid into and out of the third chamber.

In some examples, the third chamber has a longitudinal axis, an inlet, and an outlet axially spaced apart from the inlet, wherein the inlet is configured to receive the lymphatic fluid and the outlet is configured to discharge the lymphatic fluid. In some examples, the inlet and the outlet of the third chamber are each independently configured to be connected to a lymphatic vessel.

In some examples, the first chamber, the second chamber, and the third chamber (when present) are each independently formed from a model based on a tessellation of polyhedrons.

In some examples, the first chamber, the second chamber, and the third chamber (when present) are each independently formed from a computational 3D space-filling model. In some examples, the computational 3D space-filling model is a fractal space-filling model.

In some examples, the device further comprises a therapeutic agent dispersed within the hydrogel matrix. In some examples, the therapeutic agent is dispersed substantially homogeneously throughout the hydrogel matrix.

In some examples, the therapeutic agent comprises an anticancer agent, anti-inflammatory agent, antimicrobial agent, or a combination thereof. In some examples, the therapeutic agent comprises a chemotherapeutic agent, an immunotherapeutic agent, or a combination thereof.

In some examples, the first chamber is at least partially filled with adipose tissue.

In some examples, the device is implantable in a subject.

In some examples, the device is anatomically designed for the subject.

In some examples, the adipose tissue comprises autologous adipose tissue.

In some examples, the second chamber is configured to be connected to a blood vessel of the subject; the third chamber, when present, is configured to be connected to a lymphatic vessel the subject; or a combination thereof.

In some examples, the hydrogel matrix is configured to be stable for an amount of time of from 6 weeks to 12 weeks after the device is implanted in the subject.

In some examples, the hydrogel is monolithic.

In some examples, the hydrogel matrix is porous.

In some examples, the hydrogel matrix is biocompatible.

In some examples, the hydrogel matrix is biodegradable.

In some examples, the hydrogel matrix comprises a photopolymerized polymer network derived from a photosensitive polymer.

In some examples, the hydrogel matrix comprises a cross-linked polymer network derived from a photosensitive polymer.

In some examples, the hydrogel matrix comprises a plurality of layers, each layer comprising a cross-linked polymer network derived from a photosensitive polymer. In some examples, the hydrogel matrix comprises from 10 layers to 10,000 layers. In some examples, each layer independently has an average thickness of from 5 micrometers (microns, μm) to 100 μm.

In some examples, the photosensitive polymer comprises poly(ethylene glycol) diacrylate (PEGDA), poly(ethylene glycol) dimethacrylate (PEGDMA), poly(ethylene glycol) diacrylamide (PEGDAAm), gelatin methacrylate (GelMA), collagen methacrylate, silk methacrylate, hyaluronic acid methacrylate, chondroitin sulfate methacrylate, elastin methacrylate, cellulose acrylate, dextran methacrylate, heparin methacrylate, NIPAAm methacrylate, Chitosan methacrylate, polyethylene glycol norbornene, polyethylene glycol dithiol, thiolated gelatin, thiolated chitosan, thiolated silk, PEG based peptide conjugates, cell-adhesive poly(ethylene glycol), MMP-sensitive poly(ethylene glycol), PEGylated fibrinogen, or a combination thereof.

In some examples, the photosensitive polymer comprises poly(ethylene glycol) diacrylate (PEGDA).

In some examples, the photosensitive polymer has a molecular weight of from 2-50 kiloDaltons (kDa).

In some examples, the hydrogel matrix further comprises a photoabsorber. In some examples, the photoabsorber is biocompatible.

In some examples, the device is produced by additive manufacturing.

In some examples, the device is produced by stereolithography.

Also disclosed herein are methods of manufacturing any of the devices disclosed herein. In some examples, the methods comprise making the device using additive manufacturing.

In some examples, the additive manufacturing comprises stereolithography.

In some examples, the method comprises making the device based on a 3D model.

In some examples, the method further comprises using a fractal space-filling model to computationally derive the 3D model.

In some examples, the 3D model is based on an anatomical image of a subject.

In some examples, the method further comprises collecting the anatomical image of the subject.

In some examples, the method further comprises providing a pre-polymerization solution for the additive manufacturing.

In some examples, the pre-polymerization solution comprises the photosensitive polymer. In some examples, the pre-polymerization solution comprises the photosensitive polymer in an amount of from 5 wt % to 30 wt %.

In some examples, the pre-polymerization solution further comprises the photoabsorber.

In some examples, the pre-polymerization solution further comprises a solvent. In some examples, the solvent comprises water.

In some examples, the pre-polymerization solution further comprises the therapeutic agent.

In some examples, the method further comprises lining the second chamber with the plurality of cells.

Also disclosed herein are methods of treating a subject in need thereof. In some examples, the methods comprise implanting any of the devices disclosed herein into the subject.

In some examples, the first chamber is at least partially filled with adipose tissue.

In some examples, the first chamber is at least partially filled with autologous adipose tissue.

In some examples, the device is implanted into a breast of the subject.

In some examples, the method comprises breast reconstruction or augmentation.

In some examples, the method comprises connecting the second chamber to a blood vessel of the subject.

In some examples, the method comprises independently connecting the inlet and the outlet to a blood vessel of the subject.

In some examples, the method comprises connecting the third chamber to a lymphatic vessel of the subject.

In some examples, the method comprises independently connecting the inlet and the outlet of the third chamber to a lymphatic vessel of the subject.

In some examples, the method further comprises anatomically designing the device for the subject.

Additional advantages of the disclosed devices and methods will be set forth in part in the description which follows, and in part will be obvious from the description. The advantages of the disclosed devices and methods will be realized and attained by means of the elements and combinations particularly pointed out in the appended claims. It is to be understood that both the foregoing general description and the following detailed description are exemplary and explanatory only and are not restrictive of the disclosed systems and methods, as claimed.

The details of one or more embodiments of the invention are set forth in the accompanying drawings and the description below. Other features, objects, and advantages of the invention will be apparent from the description and drawings, and from the claims.

BRIEF DESCRIPTION OF THE FIGURES

The accompanying figures, which are incorporated in and constitute a part of this specification, illustrate several aspects of the disclosure, and together with the description, serve to explain the principles of the disclosure.

DETAILED DESCRIPTION

Figure 1:
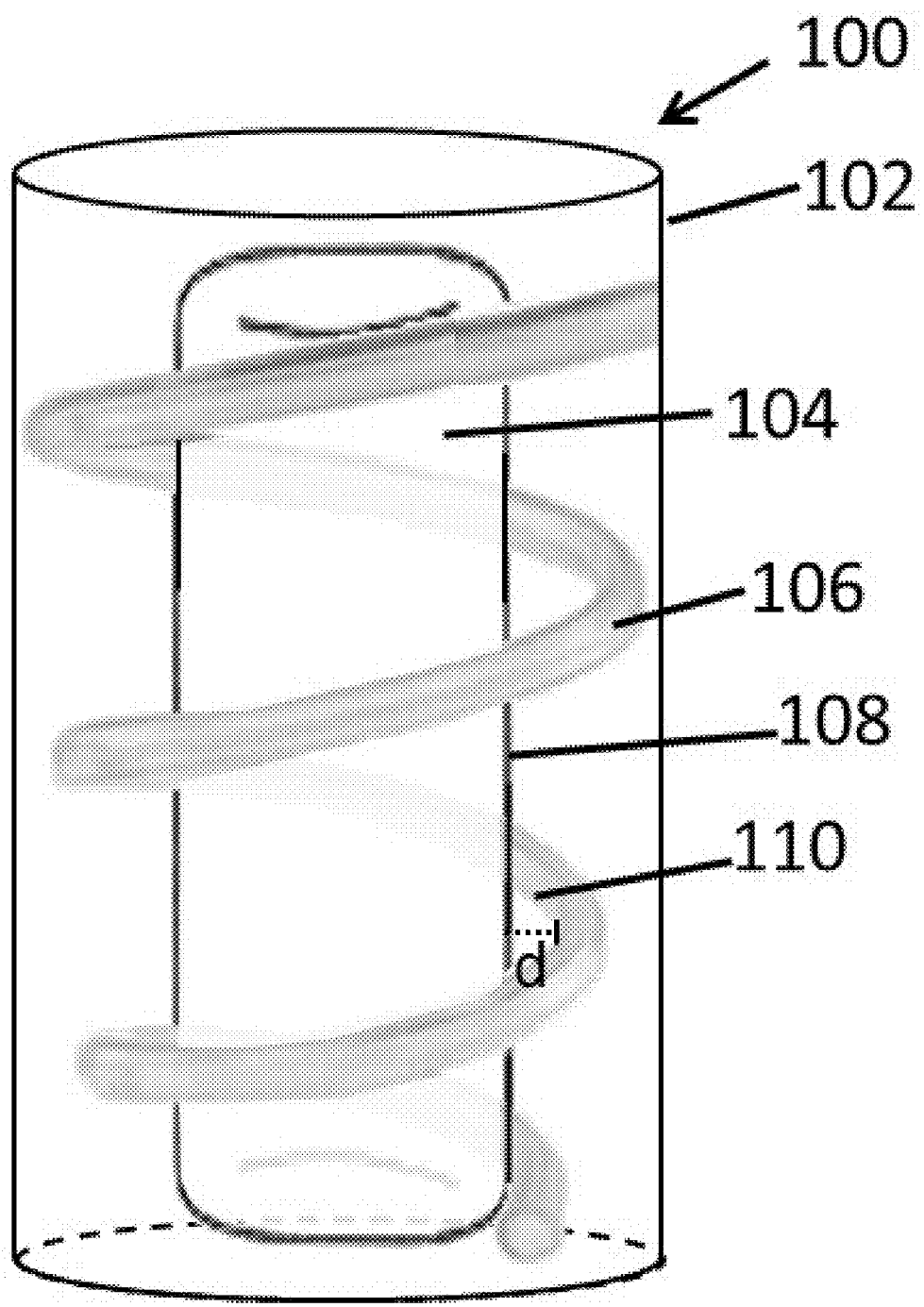
FIG. 1. Schematic view of an example hydrogel device as disclosed herein according to one implementation.

The devices and methods described herein may be understood more readily by reference to the following detailed description of specific aspects of the disclosed subject matter and the Examples included therein.

Before the present devices and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

General Definitions

In this specification and in the claims that follow, reference will be made to a number of terms, which shall be defined to have the following meanings.

Throughout the description and claims of this specification, the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a composition" includes mixtures of two or more such compositions, reference to "an agent" includes mixtures of two or more such agents, reference to "the component" includes mixtures of two or more such components, and the like.

"Optional" or "optionally" means that the subsequently described event or circumstance can or cannot occur, and that the description includes instances where the event or circumstance occurs and instances where it does not.

Ranges can be expressed herein as from "about" one particular value, and/or to "about" another particular value. By "about" is meant within 5% of the value, e.g., within 4, 3, 2, or 1% of the value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

Values can be expressed herein as an "average" value. "Average" generally refers to the statistical mean value.

By "substantially" is meant within 5%, e.g., within 4%, 3%, 2%, or 1%.

"Exemplary" means "an example of" and is not intended to convey an indication of a preferred or ideal embodiment. "Such as" is not used in a restrictive sense, but for explanatory purposes.

It is understood that throughout this specification the identifiers "first" and "second" are used solely to aid in distinguishing the various components and steps of the disclosed subject matter. The identifiers "first" and "second" are not intended to imply any particular order, amount, preference, or importance to the components or steps modified by these terms.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, by a "subject" is meant an individual. Thus, the "subject" can include domesticated animals (e.g., cats, dogs, etc.), livestock (e.g., cattle, horses, pigs, sheep, goats, etc.), laboratory animals (e.g., mouse, rabbit, rat, guinea pig, etc.), and birds. "Subject" can also include a mammal, such as a primate or a human. Thus, the subject can be a human or veterinary patient. The term "patient" refers to a subject under the treatment of a clinician, e.g., physician.

"Biocompatible" and "biologically compatible", as used herein, generally refer to compounds and/or compositions that are, along with any metabolites or degradation products thereof, generally non-toxic to normal cells and tissues, and which do not cause any significant adverse effects to normal cells and tissues when cells and tissues are incubated (e.g., cultured) in their presence.

The term "biodegradable" as used herein refers to a material or substance wherein physical dissolution and/or chemical degradation is effected under physiological conditions.

As used herein, "antimicrobial" refers to the ability to treat or control (e.g., reduce, prevent, treat, or eliminate) the growth of a microbe at any concentration. Similarly, the terms "antibacterial," "antifungal," and "antiviral" refer to the ability to treat or control the growth of bacteria, fungi, and viruses at any concentration, respectively.

As used herein, "reduce" or other forms of the word, such as "reducing" or "reduction," refers to lowering of an event or characteristic (e.g., microbe population/infection). It is understood that the reduction is typically in relation to some standard or expected value. For example, "reducing microbial infection" means reducing the spread of a microbial infection relative to a standard or a control.

As used herein, "prevent" or other forms of the word, such as "preventing" or "prevention," refers to stopping a particular event or characteristic, stabilizing or delaying the development or progression of a particular event or characteristic, or minimizing the chances that a particular event or characteristic will occur. "Prevent" does not require comparison to a control as it is typically more absolute than, for example, "reduce." As used herein, something could be reduced but not prevented, but something that is reduced could also be prevented. Likewise, something could be prevented but not reduced, but something that is prevented could also be reduced.

As used herein, "treat" or other forms of the word, such as "treated" or "treatment," refers to administration of a composition or performing a method in order to reduce, prevent, inhibit, or eliminate a particular characteristic or event (e.g., microbe growth or survival). The term "control" is used synonymously with the term "treat."

The term "anticancer" refers to the ability to treat or control cellular proliferation and/or tumor growth at any concentration.

The term "therapeutically effective" refers to the amount of the composition used is of sufficient quantity to ameliorate one or more causes or symptoms of a disease or disorder. Such amelioration only requires a reduction or alteration, not necessarily elimination.

The term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio.

As used herein, "molecular weight" refers to the number average molecular weight as measured by $^1$H NMR spectroscopy, unless indicated otherwise.

Devices

Figure 2:
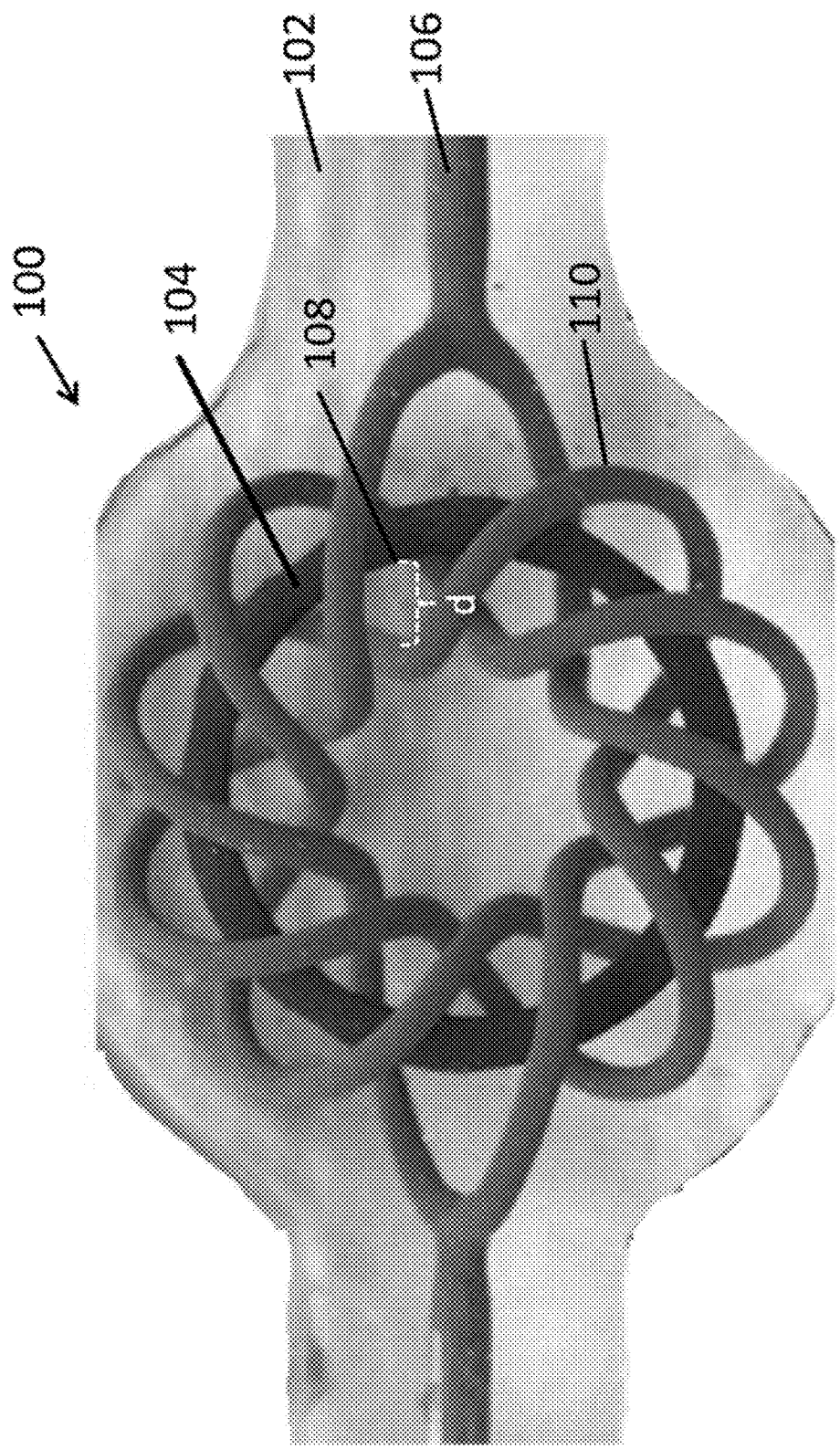
FIG. 2. Schematic view of an example hydrogel device as disclosed herein according to one implementation.
Figure 3:
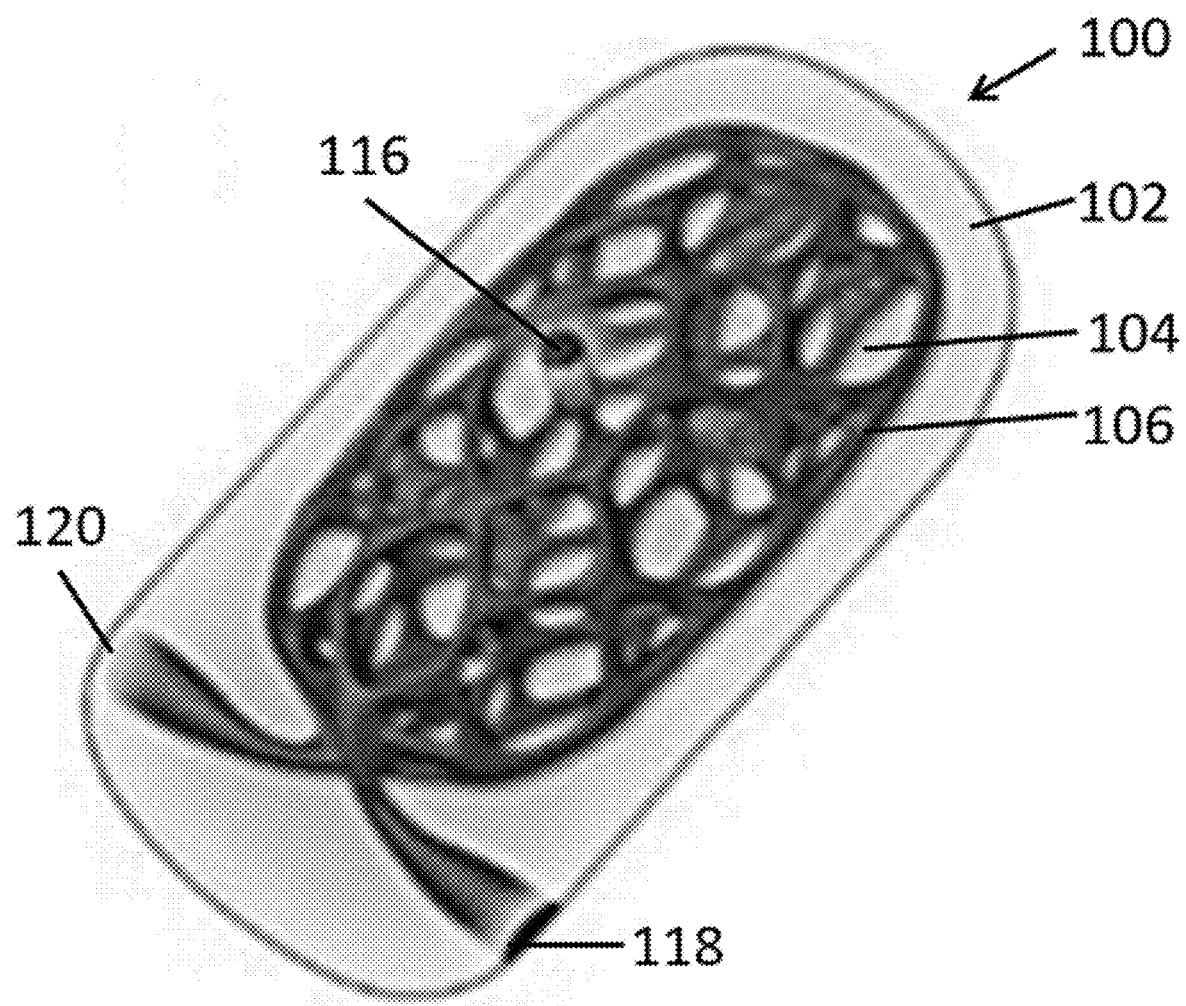
FIG. 3. Empty model of a 3D printed neobreast with blood vessels and fat chambers.
Figure 4:
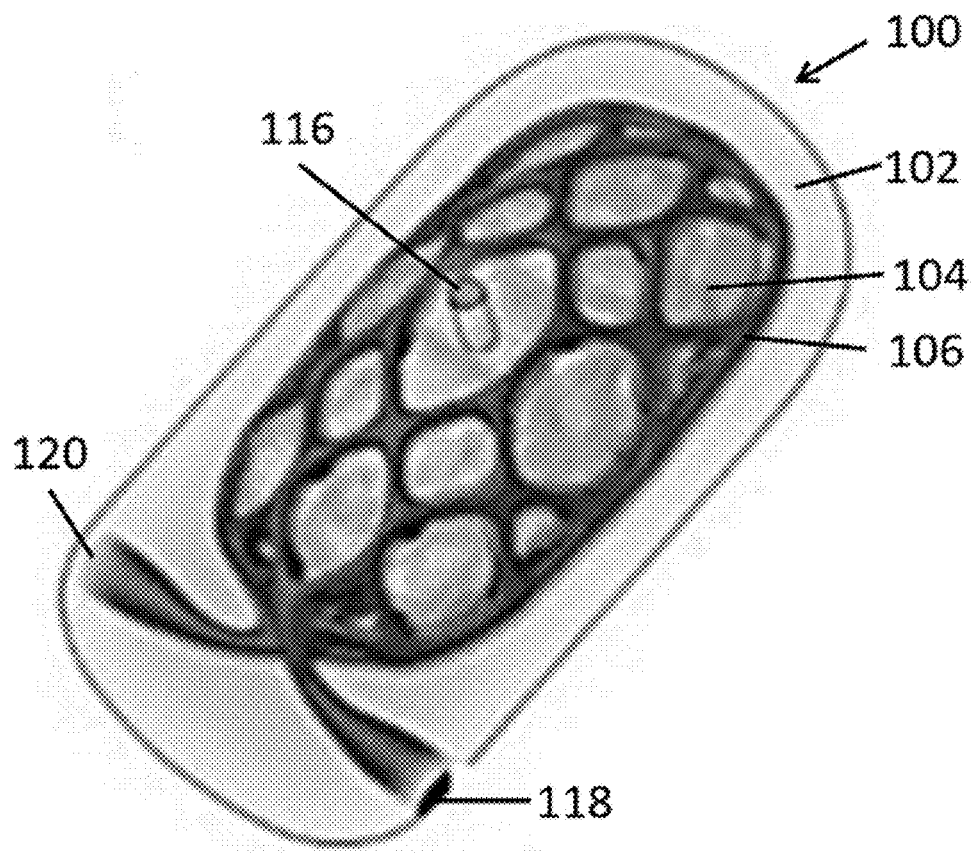
FIG. 4. Neobreast after adipocyte transplantation.
Figure 5:
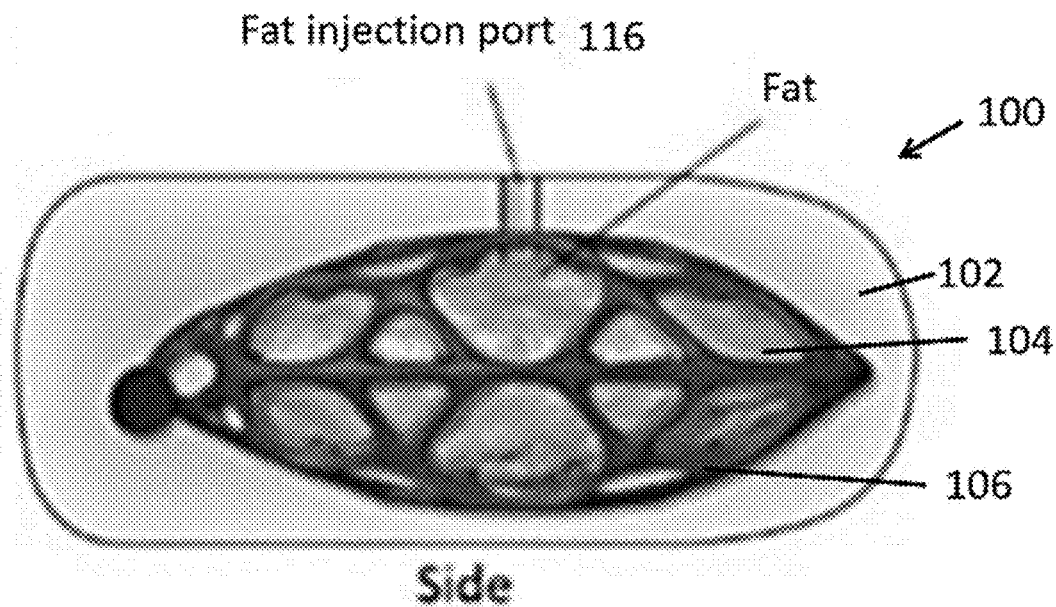
FIG. 5. Side view of neobreast showing the chambers, fat injection port, and blood vessels.

Disclosed herein are hydrogel devices. Referring now to FIG. 1-FIG. 2, in some examples, the devices 100 comprise a continuous hydrogel matrix 102; a first chamber 104 in the hydrogel matrix 102; and a second chamber 106 in the hydrogel matrix 102; wherein the first chamber 104 and the second chamber 106 are each independently perfusable; wherein the first chamber 104 is fluidly independent from the second chamber 106; wherein the first chamber 104 is configured to be at least partially filled with adipose tissue; wherein the second chamber 106 is configured to be at least partially filled with an oxygenated fluid; wherein the first chamber 104 is defined by a first border 108; wherein the second chamber 106 is defined by a second border 110; and wherein the first chamber 104 and the second chamber 106 are spaced apart from each other by an average distance (d) of from 50 micrometers (microns, µm) to 800 µm as measured from the first border 108 to the second border 110.

As used herein, a "chamber" generally refers to a volume that is at least partially enclosed, and in some instances fully enclosed, by the hydrogel matrix 102. A chamber can, for example, be hollow. In some examples, a chamber can be at least partially filled with a substance.

The first chamber 104 is defined by a first border 108. The first chamber 104 can, in some examples, be an elongated chamber. In some examples, the first chamber 104 can form a first continuous tubular channel within the hydrogel matrix 102. In some examples, the first continuous tubular channel can be branched.

"Continuous," as used herein, generally refers to a phase such that all points within the phase are directly connected three-dimensionally, so that for any two points within a continuous phase, there exists a path in three-dimensional space which connects the two points without leaving the phase.

In some examples, the first chamber 104 has a longitudinal axis. The first chamber 104 can have a cross-sectional shape in a plane perpendicular to the longitudinal axis, wherein the cross-sectional shape can be any shape, such as a regular shape, an irregular shape, an isotropic shape, or an anisotropic shape. In some examples, the cross-sectional shape of the first chamber 104 can be substantially circular, ovate, ovoid, elliptic, triangular, rectangular, polygonal, etc. In some examples, the cross-sectional shape can vary along the longitudinal axis of the first chamber 104.

The first chamber 104 can have an average characteristic dimension. The term "characteristic dimension," as used herein, refers to the largest straight-line distance between two points in the plane of the cross-sectional shape of the first chamber 104. "Average characteristic dimension" and "mean characteristic dimension" are used interchangeably herein, and generally refer to the statistical mean characteristic dimension. For example, when the first chamber 104 has a cross-sectional shape that is substantially circular and the average characteristic dimension can refer to the average diameter.

In some examples, the first chamber 104 can have an average characteristic dimension of 150 µm or more (e.g., 175 µm or more, 200 µm or more, 225 µm or more, 250 µm or more, 275 µm or more, 300 µm or more, 350 µm or more, 400 µm or more, 450 µm or more, 500 µm or more, 550 µm or more, 600 µm or more, 650 µm or more, 700 µm or more, 750 µm or more, 800 µm or more, 850 µm or more, 900 µm or more, 950 µm or more, 1 millimeter (mm) or more, 1.5 mm or more, 2 mm or more, 2.5 mm or more, 3 mm or more, 3.5 mm or more, 4 mm or more, 4.5 mm or more, 5 mm or more, 6 mm or more, 7 mm or more, 8 mm or more, or 9 mm or more). In some examples, the first chamber 104 can have an average characteristic dimension of 10 millimeters (mm) or less (e.g., 9 mm or less, 8 mm or less, 7 mm or less, 6 mm or less, 5 mm or less, 4.5 mm or less, 4 mm or less, 3.5 mm or less, 3 mm or less, 2.5 mm or less, 2 mm or less, 1.5 mm or less, 1 mm or less, 950 µm or less, 900 µm or less, 850 µm or less, 800 µm or less, 750 µm or less, 700 µm or less, 650 µm or less, 600 µm or less, 550 µm or less, 500 µm or less, 450 µm or less, 400 µm or less, 350 µm or less, 300 µm or less, 275 µm or less, 250 µm or less, 225 µm or less, or 200 µm or less). The average characteristic dimension of the first chamber 104 can range from any of the minimum values described above to any of the maximum values described above. For example, the first chamber 104 can have an average characteristic dimension of from 150 µm to 10 millimeters (mm) (e.g., from 150 µm to 1 mm, from 1 mm to 10 mm, from 150 µm to 500 µm, from 500 µm to 1 mm, from 1 mm to 5 mm, from 5 mm to 10 mm, from 175 µm to 10 mm, from 150 µm to 9 mm, from 175 µm to 9 mm, or from 300 µm to 1 mm). In some examples, the average characteristic dimension of the first chamber 104 can vary along the longitudinal axis (e.g., tapered, stepped, etc.).

The first chamber 104 is configured to be at least partially filled with adipose tissue. In some examples, the first chamber 104 further comprises an inlet 116 configured to receive the adipose tissue, for example as shown in FIG. 3-FIG. 8. In some examples, the first chamber 104 is at least partially filled with adipose tissue. In some examples, the first chamber 104 is at least partially filled with a mixture comprising adipose tissue. The mixture can, for example, further comprise an additional component, which can, for example, improve the uptake of the fat. For example, the additional component can comprise platelets, plasma, platelet-rich plasma (PRP), stem cells, a protein, or a combination thereof. In some examples, the adipose tissue comprises autologous adipose tissue.

The second chamber 106 is defined by a second border 110. The second chamber 106 can, in some examples, be an elongated chamber. In some examples, the second chamber 106 can form a second continuous tubular channel within the hydrogel matrix 102. In some examples, the second continuous tubular channel can be branched.

In some examples, the second chamber 106 has a longitudinal axis. The second chamber 106 can have a cross-sectional shape in a plane perpendicular to the longitudinal axis, wherein the cross-sectional shape can be any shape, such as a regular shape, an irregular shape, an isotropic shape, or an anisotropic shape. In some examples, the cross-sectional shape of the second chamber 106 can be substantially circular, ovate, ovoid, elliptic, triangular, rectangular, polygonal, etc. In some examples, the cross-sectional shape can vary along the longitudinal axis of the second chamber 106.

The second chamber 106 can have an average characteristic dimension. The term "characteristic dimension," as used herein, refers to the largest straight-line distance between two points in the plane of the cross-sectional shape of the second chamber 106. "Average characteristic dimension" and "mean characteristic dimension" are used interchangeably herein, and generally refer to the statistical mean characteristic dimension. For example, when the second chamber 106 has a cross-sectional shape that is substantially circular and the average characteristic dimension can refer to the average diameter.

In some examples, the second chamber 106 can have an average characteristic dimension of 5 µm or more (e.g., 10 µm or more, 15 µm or more, 20 µm or more, 25 µm or more, 30 µm or more, 35 µm or more, 40 µm or more, 45 µm or more, 50 µm or more, 60 µm or more, 70 µm or more, 80 µm or more, 90 µm or more, 100 µm or more, 125 µm or more, 150 µm or more, 175 µm or more, 200 µm or more, 225 µm or more, 250 µm or more, 275 µm or more, 300 µm or more, 375 µm or more, 400 µm or more, 425 µm or more, 450 µm or more, or 475 µm or more). In some examples, the second chamber 106 can have an average characteristic dimension of 500 µm or less (e.g., 475 µm or less, 450 µm or less, 425 µm or less, 400 µm or less, 375 µm or less, 300 µm or less, 275 µm or less, 250 µm or less, 225 µm or less, 200 µm or less, 175 µm or less, 150 µm or less, 125 µm or less, 100 µm or less, 90 µm or less, 80 µm or less, 70 µm or less, 60 µm or less, 50 µm or less, 45 µm or less, 40 µm or less, 35 µm or less, 30 µm or less, 25 µm or less, 20 µm or less, or 15 µm or less). The average characteristic dimension of the second chamber 106 can range from any of the minimum values described above to any of the maximum values described above. For example, the second chamber 106 can have an average characteristic dimension of from 5 µm to 500 µm (e.g., from 5 µm to 250 µm, from 250 µm to 500 µm, from 5 µm to 50 µm, from 50 µm to 500 µm, 5 µm to 100 µm, from 100 µm to 200 µm, from 200 µm to 300 µm from 300 µm to 400 µm, from 400 µm to 500 µm, from 10 µm to 500 µm, from 5 µm to 475 µm, from 10 µm to 475 µm, from 5 µm to 300 µm, or from 300 µm to 500 µm). In some examples, the average characteristic dimension of the second chamber 106 can vary along the longitudinal axis (e.g., tapered, stepped, etc.).

The second chamber 106 is configured to be at least partially filled with an oxygenated fluid. The oxygenated fluid can comprise any suitable oxygenated fluid. In some examples, the oxygenated fluid can comprise blood (e.g., whole blood or a component of whole blood).

In some examples, the second chamber 106 has a longitudinal axis, an inlet 118, and an outlet 120 axially spaced apart from the inlet, wherein the inlet is configured to receive the oxygenated fluid and the outlet is configured to discharge the oxygenated fluid. In some examples, the oxygenated fluid comprises blood and the inlet and the outlet of the second chamber 106 are each independently configured to be connected to a blood vessel. For example, the inlet and the outlet of the second chamber 106 can each be independently configured to be connected to an artery or a vein, e.g., the second chamber can be configured to be anastomosed using an artery-to-artery or an artery-to-vein anastomosis.

In some examples, the second chamber 106 is lined with a material that, when the oxygenated fluid comprises blood, can minimize or prevent undesired blood clotting. The material can comprise a natural or man-made material. In some examples, the second chamber 106 is lined with a plurality of cells, such as endothelial cells.

In some examples, the first chamber 104 and the second chamber 106 are entangled.

The first chamber 104 and the second chamber 106 are spaced apart from each other by an average distance of 50 micrometers (microns, µm) or more as measured from the first border 108 to the second border 110 (e.g., 75 µm or more, 100 µm or more, 125 µm or more, 150 µm or more, 175 µm or more, 200 µm or more, 225 µm or more, 250 µm or more, 275 µm or more, 300 µm or more, 325 µm or more, 350 µm or more, 375 µm or more, 400 µm or more, 425 µm or more, 450 µm or more, 475 µm or more, 500 µm or more, 550 µm or more, 600 µm or more, 650 µm or more, 700 µm or more, or 750 µm or more). In some examples, the first chamber 104 and the second chamber 106 are spaced apart from each other by an average distance of 800 micrometers (microns, µm) or less as measured from the first border 108 to the second border 110 (e.g., 750 µm or less, 700 µm or less, 650 µm or less, 600 µm or less, 550 µm or less, 500 µm or less, 475 µm or less, 450 µm or less, 425 µm or less, 400 µm or less, 375 µm or less, 350 µm or less, 325 µm or less, 300 µm or less, 275 µm or less, 250 µm or less, 225 µm or less, 200 µm or less, 175 µm or less, 150 µm or less, 125 µm or less, or 100 µm or less). The average distance that the first chamber 104 and the second chamber 106 are spaced apart from each other can range from any of the minimum values described above to any of the maximum values described above. For example, the first chamber 104 and the second chamber 106 can be spaced apart from each other by an average distance of from 50 micrometers (microns, μm) to 800 μm as measured from the first border 108 to the second border 110 (e.g., from 50 μm to 425 μm, from 425 μm to 800 μm, from 50 μm to 200 μm, from 200 μm to 400 μm, from 400 μm to 600 μm, from 600 μm to 800 μm, from 75 μm to 800 μm, from 50 μm to 750 μm, from 75 μm to 750 μm, from 50 μm to 700 μm, from 50 μm to 600 μm, from 50 μm to 500 μm, from 50 μm to 400 μm, from 100 μm to 400 μm, from 200 μm to 400 μm, from 250 μm to 350 μm, or from 275 μm to 325 μm).

Figure 6:
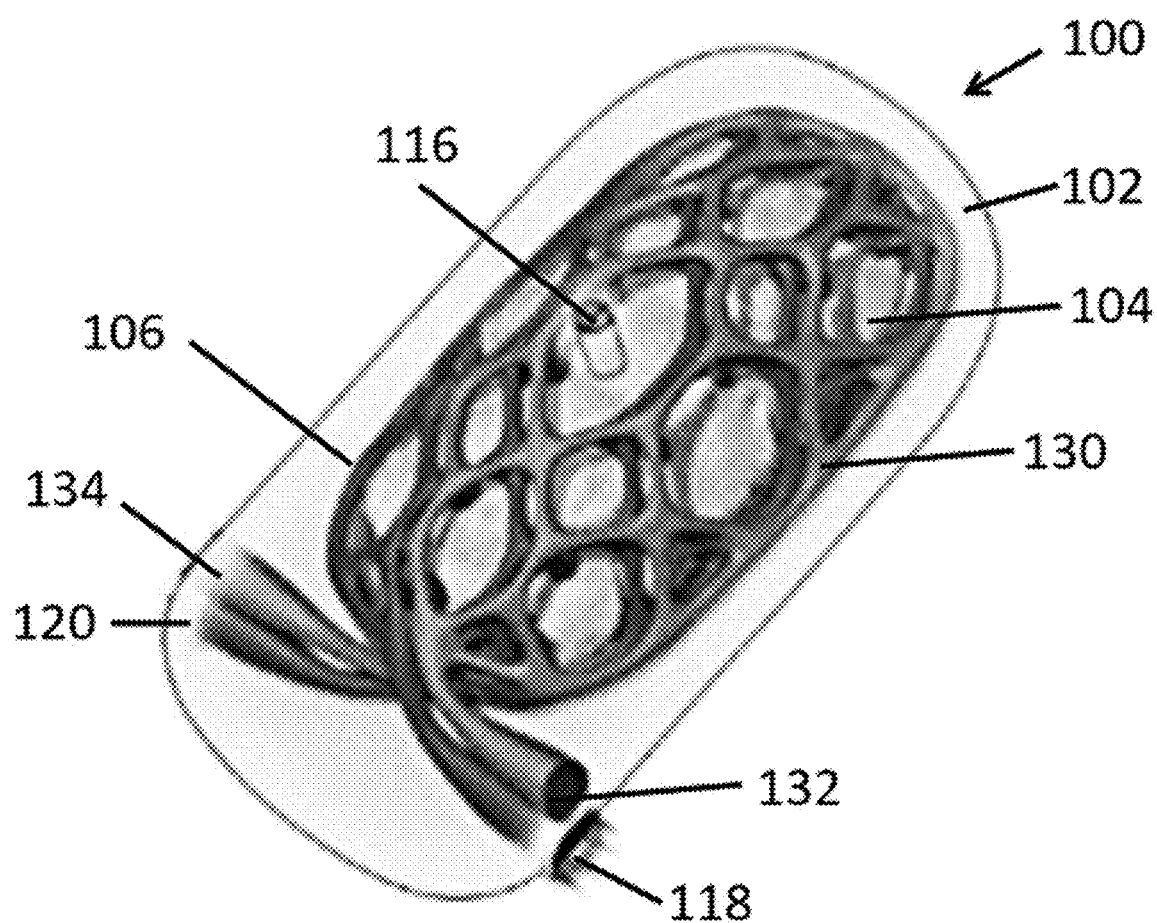
FIG. 6. Neobreast after 3D printing lymphatic channels.
Figure 7:
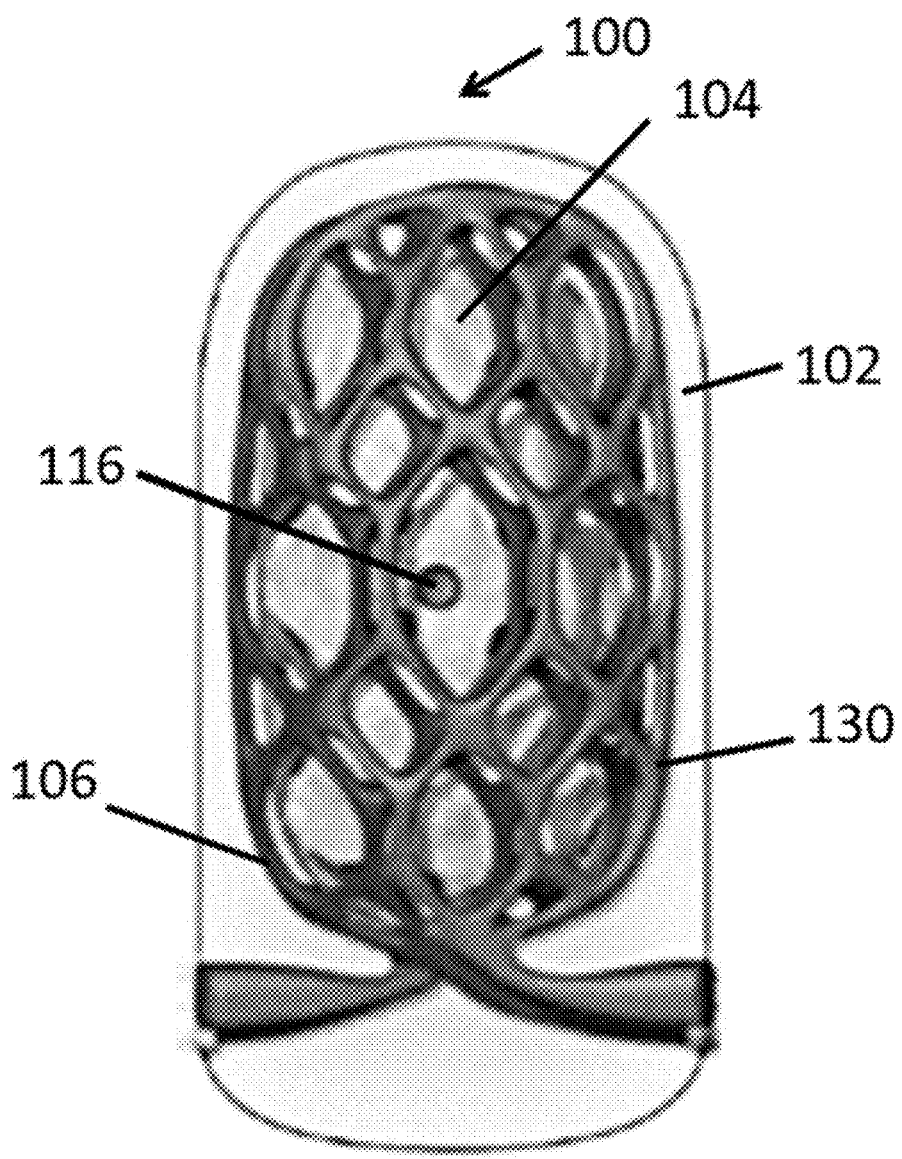
FIG. 7. Upper view of the neobreast with fat chamber, blood vessels, and lymphatic channels.
Figure 8:
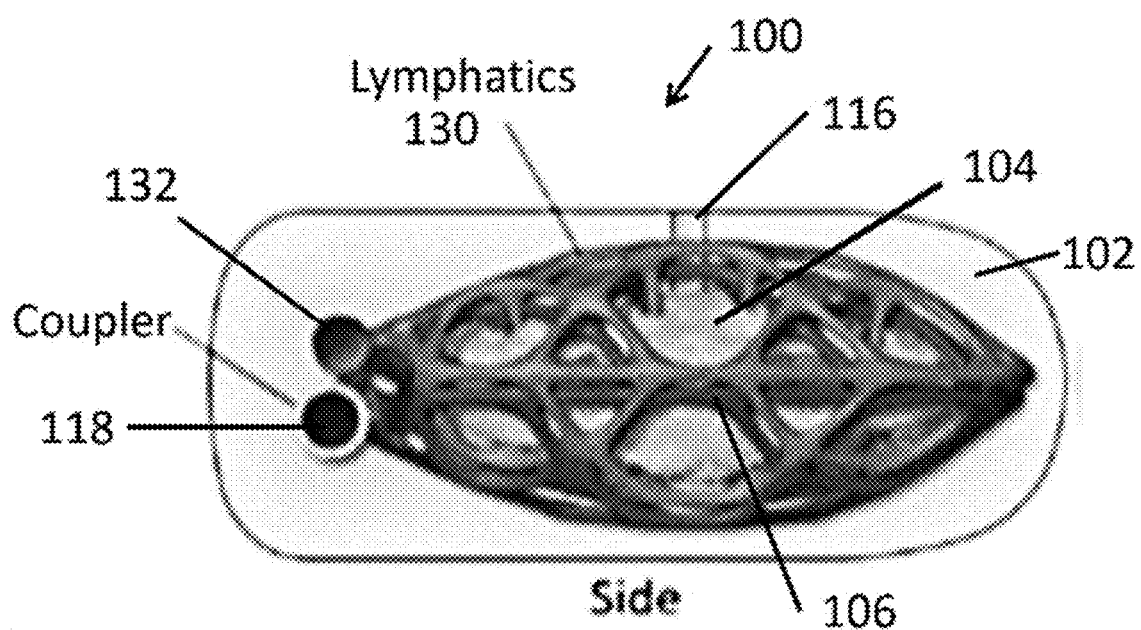
FIG. 8. Side view of the neobreast with fat chamber, blood vessels, and lymphatic channels.

In some examples, the device further comprises a third chamber 130 in the hydrogel matrix 102, wherein the third chamber 130 is perfusable and fluidly independent from the first chamber 104 and the second chamber 106. An example device comprising a third chamber is shown in FIG. 6-FIG. 8.

The third chamber is defined by a third border. The third chamber can, in some examples, be an elongated chamber. In some examples, the third chamber can form a third continuous tubular channel within the hydrogel matrix. In some examples, the third continuous tubular channel can be branched.

In some examples, the third chamber has a longitudinal axis. The third chamber can have a cross-sectional shape in a plane perpendicular to the longitudinal axis, wherein the cross-sectional shape can be any shape, such as a regular shape, an irregular shape, an isotropic shape, or an anisotropic shape. In some examples, the cross-sectional shape of the third chamber can be substantially circular, ovate, ovoid, elliptic, triangular, rectangular, polygonal, etc. In some examples, the cross-sectional shape can vary along the longitudinal axis of the third chamber.

The third chamber can have an average characteristic dimension. The term "characteristic dimension," as used herein, refers to the largest straight-line distance between two points in the plane of the cross-sectional shape of the third chamber. "Average characteristic dimension" and "mean characteristic dimension" are used interchangeably herein, and generally refer to the statistical mean characteristic dimension. For example, when the third chamber has a cross-sectional shape that is substantially circular and the average characteristic dimension can refer to the average diameter.

In some examples, the third chamber can have an average characteristic dimension of 1.5 μm or more (e.g., 2 μm or more, 2.5 μm or more, 3 μm or more, 3.5 μm or more, 4 μm or more, 4.5 μm or more, 5 μm or more, 6 μm or more, 7 μm or more, 8 μm or more, 9 μm or more, 10 μm or more, 15 μm or more, 20 μm or more, 25 μm or more, 30 μm or more, 35 μm or more, 40 μm or more, 45 μm or more, 50 μm or more, 60 μm or more, 70 μm or more, 80 μm or more, 90 μm or more, 100 μm or more, 125 μm or more, 150 μm or more, 175 μm or more, 200 μm or more, or 225 μm or more). In some examples, the third chamber can have an average characteristic dimension of 250 μm or less (e.g., 225 μm or less, 200 μm or less, 175 μm or less, 150 μm or less, 125 μm or less, 100 μm or less, 90 μm or less, 80 μm or less, 70 μm or less, 60 μm or less, 50 μm or less, 45 μm or less, 40 μm or less, 35 μm or less, 30 μm or less, 25 μm or less, 20 μm or less, 15 μm or less, 10 μm or less, 9 μm or less, 8 μm or less, 7 μm or less, 6 μm or less, 5 μm or less, 4.5 μm or less, 4 μm or less, 3.5 μm or less, 3 μm or less, or 2.5 μm or less). The average characteristic dimension of the third chamber can range from any of the minimum values described above to any of the maximum values described above. For example, the third chamber can have an average characteristic dimension of from 1.5 μm to 250 μm (e.g., from 1.5 μm to 125 μm, from 125 μm to 250 μm, from 1.5 μm to 50 μm, from 50 μm to 100 μm, from 100 μm to 150 μm from 150 μm to 200 μm, from 200 μm to 250 μm, from 1.5 μm to 225 μm, from 2.5 μm to 250 μm, from 2.5 μm to 225 μm, from 1.5 μm to 100 μm, from 100 μm to 250 μm, from 1.5 μm to 150 μm, from 150 μm to 250 μm, from 1.5 μm to 175 μm, from 2.5 μm to 175 μm, from 150 μm to 175 μm, or from 100 μm to 175 μm). In some example, the third chamber can have an average characteristic dimension that is one third to one half of the average characteristic dimension of the second chamber. In some examples, the average characteristic dimension of the third chamber can vary along the longitudinal axis (e.g., tapered, stepped, etc.).

The third chamber can be configured to be at least partially filled with a lymphatic fluid. In some examples, the third chamber further comprises a port configured to allow for the flow of the lymphatic fluid into and out of the third chamber.

In some examples, the third chamber 130 has a longitudinal axis, an inlet 132, and an outlet 134 axially spaced apart from the inlet, wherein the inlet is configured to receive the lymphatic fluid and the outlet is configured to discharge the lymphatic fluid, for example as shown in FIG. 6-FIG. 8. In some examples, the inlet and the outlet of the third chamber are each independently configured to be connected to a lymphatic vessel.

In some examples, the first chamber and the third chamber are spaced apart from each other by an average distance of 50 micrometers (microns, μm) or more as measured from the first border to the third border (e.g., 75 μm or more, 100 μm or more, 125 μm or more, 150 μm or more, 175 μm or more, 200 μm or more, 225 μm or more, 250 μm or more, 275 μm or more, 300 μm or more, 325 μm or more, 350 μm or more, 375 μm or more, 400 μm or more, 425 μm or more, 450 μm or more, 475 μm or more, 500 μm or more, 550 μm or more, 600 μm or more, 650 μm or more, 700 μm or more, or 750 μm or more). In some examples, the first chamber and the third chamber are spaced apart from each other by an average distance of 800 micrometers (microns, μm) or less as measured from the first border to the third border (e.g., 750 μm or less, 700 μm or less, 650 μm or less, 600 μm or less, 550 μm or less, 500 μm or less, 475 μm or less, 450 μm or less, 425 μm or less, 400 μm or less, 375 μm or less, 350 μm or less, 325 μm or less, 300 μm or less, 275 μm or less, 250 μm or less, 225 μm or less, 200 μm or less, 175 μm or less, 150 μm or less, 125 μm or less, or 100 μm or less). The average distance that the first chamber and the third chamber are spaced apart from each other can range from any of the minimum values described above to any of the maximum values described above. For example, the first chamber and the third chamber can be spaced apart from each other by an average distance of from 50 micrometers (microns, μm) to 800 μm as measured from the first border to the third border (e.g., from 50 μm to 425 μm, from 425 μm to 800 μm, from 50 μm to 200 μm, from 200 μm to 400 μm, from 400 μm to 600 μm, from 600 μm to 800 μm, from 75 μm to 800 μm, from 50 μm to 750 μm, from 75 μm to 750 μm, from 50 μm to 700 μm, from 50 μm to 600 μm, from 50 μm to 500 μm, from 50 μm to 400 μm, from 100 μm to 400 μm, from 200 μm to 400 μm, from 250 μm to 350 μm, or from 275 μm to 325 μm).

In some examples, the second chamber and the third chamber are spaced apart from each other by an average distance of 1 micrometer (micron, μm) or more as measured from the second border to the third border (e.g., 2 μm or more, 3 μm or more, 4 μm or more, 5 μm or more, 10 μm or more, 15 μm or more, 20 μm or more, 25 μm or more, 30 μm or more, 40 µm or more, 50 µm or more, 75 µm or more, 100 µm or more, 125 µm or more, 150 µm or more, 175 µm or more, 200 µm or more, 225 µm or more, 250 µm or more, 275 µm or more, 300 µm or more, 325 µm or more, 350 µm or more, 375 µm or more, 400 µm or more, 425 µm or more, 450 µm or more, 475 µm or more, 500 µm or more, 550 µm or more, 600 µm or more, 650 µm or more, 700 µm or more, or 750 µm or more). In some examples, the second chamber and the third chamber are spaced apart from each other by an average distance of 800 micrometers (microns, µm) or less as measured from the second border to the third border (e.g., 750 µm or less, 700 µm or less, 650 µm or less, 600 µm or less, 550 µm or less, 500 µm or less, 475 µm or less, 450 µm or less, 425 µm or less, 400 µm or less, 375 µm or less, 350 µm or less, 325 µm or less, 300 µm or less, 275 µm or less, 250 µm or less, 225 µm or less, 200 µm or less, 175 µm or less, 150 µm or less, 125 µm or less, 100 µm or less, 75 µm or less, 50 µm or less, 40 µm or less, 30 µm or less, 25 µm or less, 20 µm or less, 15 µm or less, 10 µm or less, or 5 µm or less). The average distance that the second chamber and the third chamber are spaced apart from each other can range from any of the minimum values described above to any of the maximum values described above. For example, the second chamber and the third chamber can be spaced apart from each other by an average distance of from 1 micrometer (micron, µm) to 800 µm as measured from the second border to the third border (e.g., from 1 µm to 400 µm, from 400 µm to 800 µm, from 1 µm to 200 µm, from 200 µm to 400 µm, from 400 µm to 600 µm, from 600 µm to 800 µm, from 5 µm to 800 µm, from 1 µm to 750 µm, or from 5 µm to 750 µm).

In some examples, the third chamber can be similar to the second chamber in geometry. In some examples, the third chamber can mirror the second chamber in geometry.

In some examples, the third chamber is entangled with the first chamber and/or the second chamber.

In some examples, the first chamber, the second chamber, the third chamber (when present), or a combination thereof, can each independently be formed from a model based on a tessellation of polyhedrons. For example, the first chamber, the second chamber, the third chamber (when present), or a combination thereof can each independently be formed from a computational 3D space-filling model. For example, the second chamber and/or the third chamber (when present) can each independently be formed from a computational 3D space-filling model to maximize the surface area while minimizing flow resistance and providing for robust mass transport. The computational 3D space-filling model can, for example, be a fractal space-filling model.

In some examples, the hydrogel matrix is monolithic. In some examples, the hydrogel matrix is porous. In some examples, the hydrogel matrix is biocompatible, biodegradable, or a combination thereof.

In some examples, the hydrogel matrix comprises a photopolymerized polymer network derived from a photosensitive polymer. In some examples, the hydrogel matrix comprises a cross-linked polymer network derived from a photosensitive polymer. In some examples, the hydrogel matrix comprises a plurality of layers, each layer comprising a cross-linked polymer network derived from a photosensitive polymer.

In some examples, the hydrogel matrix can comprise 10 layers or more (e.g., 15 layers or more; 20 layers or more; 25 layers or more; 30 layers or more; 35 layers or more; 40 layers or more; 45 layers or more; 50 layers or more; 60 layers or more; 70 layers or more; 80 layers or more; 90 layers or more; 100 layers or more; 125 layers or more; 150 layers or more; 175 layers or more; 200 layers or more; 225 layers or more; 250 layers or more; 275 layers or more; 300 layers or more; 325 layers or more; 350 layers or more; 375 layers or more; 400 layers or more; 425 layers or more; 450 layers or more; 475 layers or more; 500 layers or more; 550 layers or more; 600 layers or more; 650 layers or more; 700 layers or more; 750 layers or more; 800 layers or more; 850 layers or more; 900 layers or more; 950 layers or more; 1,000 layers or more; 1,250 layers or more; 1,500 layers or more; 1,750 layers or more; 2,000 layers or more; 2,250 layers or more; 2,500 layers or more; 2,750 layers or more; 3,000 layers or more; 3,250 layers or more; 3,750 layers or more; 4,000 layers or more; 4,250 layers or more; 4,500 layers or more; 4,750 layers or more; 5,000 layers or more; 5,500 layers or more; 6,000 layers or more; 6,500 layers or more; 7,000 layers or more; 7,500 layers or more; 8,000 layers or more; 8,500 layers or more; or 9,000 layers or more).

In some examples, the hydrogel matrix can comprise 10,000 layers or less (e.g., 9,500 layers or less; 9,000 layers or less; 8,500 layers or less; 8,000 layers or less; 7,500 layers or less; 7,000 layers or less; 6,500 layers or less; 6,000 layers or less; 5,500 layers or less; 5,000 layers or less; 4,750 layers or less; 4,500 layers or less; 4,250 layers or less; 4,000 layers or less; 3,750 layers or less; 3,500 layers or less; 3,250 layers or less; 3,000 layers or less; 2,750 layers or less; 2,500 layers or less; 2,250 layers or less; 2,000 layers or less; 1,750 layers or less; 1,500 layers or less; 1,250 layers or less; 1,000 layers or less; 950 layers or less; 900 layers or less; 850 layers or less; 800 layers or less; 750 layers or less; 700 layers or less; 650 layers or less; 600 layers or less; 550 layers or less; 500 layers or less; 475 layers or less; 450 layers or less; 425 layers or less; 400 layers or less; 375 layers or less; 350 layers or less; 325 layers or less; 300 layers or less; 275 layers or less; 250 layers or less; 225 layers or less; 200 layers or less; 175 layers or less; 150 layers or less; 125 layers or less; 100 layers or less; 90 layers or less; 80 layers or less; 70 layers or less; 60 layers or less; 50 layers or less; 45 layers or less; 40 layers or less; 35 layers or less; 30 layers or less; 25 layers or less; or 20 layers or less).

The number of layers comprising the hydrogel matrix can range from any of the minimum values described above to any of the maximum values described above. For example, the hydrogel matrix can comprise from 10 layers to 10,000 layers (e.g., from 10 layers to 100 layers; from 100 layers to 1,000 layers; from 1,000 layer to 10,000 layers; from 10 layers to 2,000 layers; from 2,000 layers to 4,000 layers; from 4,000 layers to 6,000 layers; from 6,000 layers to 8,000 layers; from 8,000 layers to 10,000 layers; from 10 layers to 9,000 layers; from 20 layers to 10,000 layers; or from 20 layers to 9,000 layers).

Each layer can independently have an average thickness of 5 µm or more (e.g., 6 µm or more, 7 µm or more, 8 µm or more, 9 µm or more, 10 µm or more, 15 µm or more, 20 µm or more, 25 µm or more, 30 µm or more, 35 µm or more, 40 µm or more, 45 µm or more, 50 µm or more, 55 µm or more, 60 µm or more, 65 µm or more, 70 µm or more, 75 µm or more, 80 µm or more, 85 µm or more, 90 µm or more, or 95 µm or more). In some examples, each layer can independently have an average thickness of 100 µm or less (e.g., 95 µm or less, 90 µm or less, 85 µm or less, 80 µm or less, 75 µm or less, 70 µm or less, 65 µm or less, 60 µm or less, 55 µm or less, 50 µm or less, 45 µm or less, 40 µm or less, 35 µm or less, 30 µm or less, 25 µm or less, 20 µm or less, 15 µm or less, or 10 µm or less). The average thickness of each of the layers can independently range from any of the minimum values described above to any of the maximum values described above. For example, each layer can independently have an average thickness of from 5 micrometers (microns, µm) to 100 µm (e.g., from 5 µm to 50 µm, from 50 µm to 100 µm, from 5 µm to 25 µm, from 25 µm to 50 µm, from 50 µm to 75 µm, from 75 µm to 100 µm, from 5 µm to 90 µm, from 10 µm to 100 µm, from 10 µm to 90 µm, or from 25 µm to 100 µm). In some examples, each layer can have substantially the same average thickness.

The photosensitive polymer can comprise any suitable material. For example, the photosensitive polymer can comprise poly(ethylene glycol) diacrylate (PEGDA), poly(ethylene glycol) dimethacrylate (PEGDMA), poly(ethylene glycol) diacrylamide (PEGDAAm), gelatin methacrylate (GelMA), collagen methacrylate, silk methacrylate, hyaluronic acid methacrylate, chondroitin sulfate methacrylate, elastin methacrylate, cellulose acrylate, dextran methacrylate, heparin methacrylate, NIPAAm methacrylate, Chitosan methacrylate, polyethylene glycol norbornene, polyethylene glycol dithiol, thiolated gelatin, thiolated chitosan, thiolated silk, PEG based peptide conjugates, cell-adhesive poly(ethylene glycol), MMP-sensitive poly(ethylene glycol), PEGylated fibrinogen, or a combination thereof. In some examples, the photosensitive polymer comprises poly(ethylene glycol) diacrylate (PEGDA).

The photosensitive polymer can, for example, have a molecular weight of 2 kiloDaltons (kDa) or more (e.g., 3 kDa or more, 4 kDa or more, 5 kDa or more, 6 kDa or more, 7 kDa or more, 8 kDa or more, 9 kDa or more, 10 kDa or more, 15 kDa or more, 20 kDa or more, 25 kDa or more, 30 kDa or more, 35 kDa or more, 40 kDa or more, or 45 kDa or more). In some examples, the photosensitive polymer can have a molecular weight of 50 kDa or less (e.g., 45 kDa or less, 40 kDa or less, 35 kDa or less, 30 kDa or less, 25 kDa or less, 20 kDa or less, 15 kDa or less, 10 kDa or less, 9 kDa or less, 8 kDa or less, 7 kDa or less, 6 kDa or less, 5 kDa or less, or 4 kDa or less). The molecular weight of the photosensitive polymer can range from any of the minimum values described above to any of the maximum values described above. For example, the photosensitive polymer can have a molecular weight of from 2 kDa to 50 kDa (e.g., from 2 kDa to 25 kDa, from 25 kDa to 50 kDa, from 2 kDa to 10 kDa, from 10 kDa to 20 kDa, from 20 kDa to 30 kDa, from 30 kDa to 40 kDa, from 40 kDa to 50 kDa, from 2 kDa to 45 kDa, from 4 kDa to 50 kDa, from 4 kDa to 45 kDa, or from 4 kDa to 8 kDa).

In some examples, the hydrogel matrix further comprises a photoabsorber. In some examples, the photoabsorber is biocompatible. In some examples, the photoabsorber is degradable independent of any degradation of the hydrogel matrix.

Possible photoabsorbers can be one or more food dyes including tartrazine, Sunset Yellow FCF (Yellow No. 6), Brilliant Blue FCF (FD&C Blue No. 1), Indigo Carmine (FD&C Blue No. 2), Fast Green FCF (FD&C Green No. 3) anthocyanins, anthocyanidin, erythrosine (FD&C Red No. 3), Allura Red AC (FD&C Red No. 40), riboflavin (Vitamin B2, E101, E101a, E106), ascorbic acid (vitamin C), Quinoline Yellow WS, carmoisine (azorubine), Ponceau 4R (E124), Patent Blue V (E131), Green S (E142), Yellow 2G (E107), Orange GGN (E111), Red 2G (E128), caramel color, phenol red, methyl orange, 4-nitrophenol, and NADH disodium salt. Also possible are curcumin (E100), turmeric, alpha-carotene, beta carotene, canthaxanthin (keto-carotenoid), cochineal extract, paprika, saffron, ergocalciferol (vitamin D2), cholecalciferol (vitamin D3), Citrus Red 2, annatto extract, and lycopene. In some examples, the photoabsorber can comprise a metallic particle, such as gold nanoparticles, silver nanoparticles, or a combination thereof.

In some examples, the device further comprises a therapeutic agent dispersed within the hydrogel matrix. In some examples, the therapeutic agent is dispersed inhomogeneously throughout the hydrogel matrix (e.g., randomly, along a concentration gradient, etc.). In some examples, the therapeutic agent is dispersed substantially homogeneously throughout the hydrogel matrix.

The therapeutic agent can, for example, comprise an anticancer agent, anti-inflammatory agent, antimicrobial agent, or a combination thereof. As used herein, antimicrobials include, for example, antibacterials, antifungals, and antivirals.

Examples of antimicrobial agents include, but are not limited to, alexidine, asphodelin A, atromentin, auranthine, austrocortilutein, austrocortirubin, azerizin, chlorbisan, chloroxine, cidex, cinoxacin, citreorosein, copper usnate, cupiennin, curvularin, DBNPA, dehydrocurvularin, desoxyfructo-serotonin, dichloroisocyanuric acid, elaiomycin, holtfreter's solution, malettinin, naphthomycin, neutrolin, niphimycin, nitrocefin, oxadiazoles, paenibacterin, proclin, ritiometan, ritipenem, silicone quaternary amine, stylisin, taurolidine, tirandamycin, trichloroisocyanuric acid, triclocarban, and combinations thereof.

Examples of antibacterials include, but are not limited to, acetoxycycloheximide, aciduliprofundum, actaplanin, actinorhodin, alazopeptin, albomycin, allicin, allistatin, allyl isothiocyanate, ambazone, aminocoumarin, aminoglycosides, 4-aminosalicylic acid, ampicillin, ansamycin, anthramycin, antimycin A, aphidicolin, aplasmomycin, archaeocin, arenicin, arsphenamine, arylomycin A2, ascofuranone, aspergillic acid, avenanthramide, avibactam, azelaic acid, bafilomycin, bambermycin, beauvericin, benzoyl peroxide, blasticidin S, bottromycin, brilacidin, caprazamycin, carbomycin, cathelicidin, cephalosporins, ceragenin, chartreusin, chromomycin A3, citromycin, clindamycin, clofazimine, clofoctol, clorobiocin, coprinol, coumermycin A1, cyclic lipopeptides, cycloheximide, cycloserine, dalfopristin, dapsone, daptomycin, debromomarinone, 17-dimethylaminoethylamino-17-demethoxygeldanamycin, echinomycin, endiandric acid C, enediyne, enviomycin, eravacycline, erythromycin, esperamicin, etamycin, ethambutol, ethionamide, (6S)-6-fluoroshikimic acid, fosfomycin, fosmidomycin, friulimicin, furazolidone, furonazide, fusidic acid, geldanamycin, gentamycin, gepotidacin, glycyclclines, glycyrrhizol, gramicidin S, guanacastepene A, hachimycin, halocyamine, hedamycin, helquinoline, herbimycin, hexamethylenetetramine, hitachimycin, hydramacin-1, isoniazid, kanamycin, katanosin, kedarcidin, kendomycin, kettapeptin, kidamycin, lactivicin, lactocillin, landomycin, landomycinone, lasalocid, lenapenem, leptomycin, lincosamides, linopristin, lipiarmycins, macbecin, macrolides, macromomycin B, maduropeptin, mannopeptimycin glycopeptide, marinone, meclocycline, melafix, methylenomycin A, methylenomycin B, monensin, moromycin, mupirocin, mycosubtilin, myriocin, myxopyronin, naphthomycin A, narasin, neocarzinostatin, neopluramycin, neosalvarsan, neothramycin, netropsin, nifuroxazide, nifurquinazol, nigericin, nitrofural, nitrofurantoin, nocathiacin I, novobiocin, omadacycline, oxacephem, oxazolidinones, penicillins, peptaibol, phytoalexin, plantazolicin, platensimycin, plectasin, pluramycin A, polymixins, polyoxins, pristinamycin, pristinamycin IA, promin, prothionamide, pulvinone, puromycin, pyocyanase, pyocyanin, pyrenocine, questiomycin A, quinolones, quinupristin, ramoplanin, raphanin, resistome, reuterin, rifalazil, rifamycins, ristocetin, roseophilin, salinomycin, salinosporamide A, saptomycin, saquayamycin, seraticin, sideromycin, sodium sulfacetamide, solasulfone, solithromycin, sparassol, spectinomycin, staurosporine, streptazolin, streptogramin, streptogramin B, streptolydigin, streptonigrin, styelin A, sulfonamides, surfactin, surotomycin, tachyplesin, taksta, tanespimycin, telavancin, tetracyclines, thioacetazone, thiocarlide, thiolutin, thiostrepton, tobramycin, trichostatin A, triclosan, trimethoprim, trimethoprim, tunicamycin, tyrocidine, urauchimycin, validamycin, viridicatumtoxin B, vulgamycin, xanthomycin A, xibornol, amikacin, amoxicillin, ampicillin, atovaquone, azithromycin, aztreonam, bacitracin, carbenicillin, cefadroxil, cefazolin, cefdinir, cefditoren, cefepime, cefiderocol, cefoperazone, cefotetan, cefoxitin, cefotaxime, cefpodoxime, cefprozil, ceftaroline, ceftazidime, ceftibuten, ceftizoxime, ceftriaxone, chloramphenicol, colistimethate, cefuroxime, cephalexin, cephradine, cilastatin, cinoxacin, ciprofloxacin, clarithromycin, clindamycin, dalbavancin, dalfopristin, daptomycin, demeclocycline, dicloxacillin, doripenem, doxycycline, eravacycline, ertapenem, erythromycin, fidaxomicin, fosfomycin, gatifloxacin, gemifloxacin, gentamicin, imipenem, lefamulin, lincomycin, linezolid, lomefloxacin, loracarbef, meropenem, metronidazole, minocycline, moxifloxacin, nafcillin, nalidixic acid, neomycin, norfloxacin, ofloxacin, omadacycline, oritavancin, oxacillin, oxytetracycline, paromomycin, penicillin, pentamidine, piperacillin, plazomicin, quinupristin, rifaximin, sarecycline, secnidazole, sparfloxacin, spectinomycin, sulfamethoxazole, sulfisoxazole, tedizolid, telavancin, telithromycin, ticarcillin, tigecycline, tobramycin, trimethoprim, trovafloxacin, vancomycin, and combinations thereof.

Examples of antifungals include, but are not limited to, abafungin, acibenzolar, acibenzolar-S-methyl, acrisorcin, allicin, aminocandin, amorolfine, amphotericin B, anidulafungin, azoxystrobin, bacillomycin, *Bacillus pumilus*, barium borate, benomyl, binapacryl, boric acid, bromine monochloride, bromochlorosalicylanilide, bupirimate, butenafine, candicidin, caprylic acid, captafol, captan, carbendazim, caspofungin, cerulenin, chloranil, chlormidazole, chlorophetanol, chlorothalonil, chloroxylenol, chromated copper arsenate, ciclopirox, cilofungin, cinnamaldehyde, clioquinol, copper(I) cyanide, copper(II) arsenate, cruentaren, cycloheximide, davicil, dehydroacetic acid, dicarboximide fungicides, dichlofluanid, dimazole, diphenylamine, echinocandin, echinocandin B, epoxiconazole, ethonam, falcarindiol, falcarinol, famoxadone, fenamidone, fenarimol, fenpropimorph, fentin acetate, fenticlor, filipin, fluazinam, fluopicolide, flusilazole, fluxapyroxad, fuberidazole, griseofulvin, halicylindramide, haloprogin, hamycin, hexachlorobenzene, hexachlorocyclohexa-2,5-dien-1-one, 5-hydroxy-2(5H)-furanone, iprodione, lime sulfur, mancozeb, maneb, melafix, metalaxyl, metam sodium, methylisothiazolone, methylparaben, micafungin, miltefosine, monosodium methyl arsenate, mycobacillin, myclobutanil, natamycin, beta-nitrostyrene, nystatin, paclobutrazol, papulacandin B, parietin, pecilocin, pencycuron, pentamidine, pentachloronitrobenzene, pentachlorophenol, perimycin, 2-phenylphenol, polyene antimycotic, propamocarb, propiconazole, pterulone, ptilomycalin A, pyrazophos, pyrimethanil, pyrrolnitrin, selenium disulfide, sparassol, strobilurin, sulbentine, tavaborole, tebuconazole, terbinafine, theonellamide F, thymol, tiabendazole, ticlatone, tolciclate, tolnaftate, triadimefon, triamiphos, tribromometacresol, 2,4,6-tribromophenol, tributyltin oxide, triclocarban, triclosan, tridemorph, trimetrexate, undecylenic acid, validamycin, venturicidin, vinclozolin, vinyldithiin, vusion, xanthene, zinc borate, zinc pyrithione, zineb, ziram, voriconazole, itraconazole, posaconazole, fluconazole, ketoconazole, clotrimazole, isavuconazonium, miconazole, caspofungin, anidulafungin, micafungin, griseofulvin, terbinafine, flucytosine, terbinafine, nystatin, amphotericin b., and combinations thereof.

Examples of antivirals include, but are not limited to, afovirsen, alisporivir, angustific acid, angustifodilactone, alovudine, beclabuvir, 2,3-bis(acetylmercaptomethyl)quinoxaline, brincidofovir, dasabuvir, docosanol, fialuridine, ibacitabine, imiquimod, inosine, inosine pranobex, interferon, metisazone, miltefosine, neokadsuranin, neotripterifordin, ombitasvir, oragen, oseltamivir, pegylated interferon, podophyllotoxin, radalbuvir, semapimod, tecovirimat, telbivudine, theaflavin, tilorone, triptofordin C-2, variecolol, Zmapp, abacavir, acyclovir, adefovir, amantadine, amprenavir, atazanavir, balavir, baloxavir marboxil, boceprevir, cidofovir, cobicistat, daclatasvir, darunavir, delavirdine, didanosine, docasanol, dolutegravir, doravirine, ecoliever, edoxudine, efavirenz, elvitegravir, emtricitabine, enfuvirtide, entecavir, etravirine, famciclovir, fomivirsen, fosamprenavir, forscarnet, fosnonet, famciclovir, favipravir, fomivirsen, foscavir, ganciclovir, ibacitabine, idoxuridine, indinavir, inosine, inosine pranobex, interferon type I, interferon type II, interferon type III, lamivudine, letermovir, letermovir, lopinavir, loviride, maraviroc, methisazone, moroxydine, nelfinavir, nevirapine, nitazoxanide, oseltamivir, peginterferon alfa-2a, peginterferon alfa-2b, penciclovir, peramivir, pleconaril, podophyllotoxin, pyramidine, raltegravir, remdesevir, ribavirin, rilpivirine, rimantadine, rintatolimod, ritonavir, saquinavir, simeprevir, sofosbuvir, stavudine, tarabivirin, telaprevir, telbivudine, tenofovir alafenamide, tenofovir disoproxil, tenofovir, tipranavir, trifluridine, trizivir, tromantadine, umifenovir, valaciclovir, valganciclovir, vidarabine, zalcitabine, zanamivir, zidovudine. And combinations thereof.

In some examples, the therapeutic agent can comprise an anticancer agent. In some examples, the therapeutic agent comprises a chemotherapeutic agent, an immunotherapeutic agent, or a combination thereof.

In some examples, the therapeutic agent can comprise a chemotherapeutic agent. Chemotherapy is the treatment of cancer with one or more cytotoxic anti-neoplastic drugs (e.g., chemotherapeutic agents) as part of a standardized regimen. Chemotherapy may be given with a curative intent or it may aim to prolong life or to palliate symptoms. In some cases, it can be used in conjunction with other cancer treatments, such as radiation therapy, surgery, hyperthermia therapy, or a combination thereof. Examples of chemotherapeutic agents include, but are not limited to, 13-cis-Retinoic Acid, 2-Amino-6-Mercaptopurine, 2-CdA, 2-Chlorodeoxyadenosine, 5-fluorouracil, 6-Thioguanine, 6-Mercaptopurine, Accutane, Actinomycin-D, Adriamycin, Adrucil, Agrylin, Ala-Cort, Aldesleukin, Alemtuzumab, Alitretinoin, Alkaban-AQ, Alkeran, All-transretinoic acid, Alpha interferon, Altretamine, Amethopterin, Amifostine, Aminoglutethimide, Anagrelide, Anandron, Anastrozole, Arabinosylcytosine, Aranesp, Aredia, Arimidex, Aromasin, Arsenic trioxide, Asparaginase, ATRA, Avastin, BCG, BCNU, Bevacizumab, Bexarotene, Bicalutamide, BiCNU, Blenoxane, Bleomycin, Bortezomib, Busulfan, Busulfex, C225, Calcium Leucovorin, Campath, Camptosar, Camptothecin-11, Capecitabine, Carac, Carboplatin, Carmustine, Carmustine wafer, Casodex, CCNU, CDDP, CeeNU, Cerubidine, cetuximab, Chlorambucil, Cisplatin, Citrovorum Factor, Cladribine, Cortisone, Cosmegen, CPT-11, Cyclophosphamide, Cytadren, Cytarabine, Cytarabine liposomal, Cytosar-U, Cytoxan, Dacarbazine, Dactinomycin, Darbepoetin alfa, Daunomycin, Daunorubicin, Daunorubicin hydrochloride, Daunorubicin liposomal, DaunoXome, Decadron, Delta-Cortef, Deltasone, Denileukin diftitox, DepoCyt, Dexamethasone, Dexamethasone acetate, Dexamethasone sodium phosphate, Dexasone, Dexrazoxane, DHAD, DIC, Diodex, Docetaxel, Doxil, Doxorubicin, Doxorubicin liposomal, Droxia, DTIC, DTIC-Dome, Duralone, Efudex, Eligard, Ellence, Eloxatin, Elspar, Emcyt, Epirubicin, Epoetin alfa, Erbitux, Erwinia L-asparaginase, Estramustine, Ethyol, Etopophos, Etoposide, Etoposide phosphate, Eulexin, Evista, Exemestane, Fareston, Faslodex, Femara, Filgrastim, Floxuridine, Fludara, Fludarabine, Fluoroplex, Fluorouracil, Fluorouracil (cream), Fluoxymesterone, Flutamide, Folinic Acid, FUDR, Fulvestrant, G-CSF, Gefitinib, Gemcitabine, Gemtuzumab ozogamicin, Gemzar, Gleevec, Lupron, Lupron Depot, Matulane, Maxidex, Mechlorethamine, Mechlorethamine Hydrochlorine, Medralone, Medrol, Megace, Megestrol, Megestrol Acetate, Melphalan, Mercaptopurine, Mesna, Mesnex, Methotrexate, Methotrexate Sodium, Methylprednisolone, Mylocel, Letrozole, Neosar, Neulasta, Neumega, Neupogen, Nilandron, Nilutamide, Nitrogen Mustard, Novaldex, Novantrone, Octreotide, Octreotide acetate, Oncospar, Oncovin, Ontak, Onxal, Oprevelkin, Orapred, Orasone, Oxaliplatin, Paclitaxel, Pamidronate, Panretin, Paraplatin, Pediapred, PEG Interferon, Pegaspargase, Pegfilgrastim, PEG-INTRON, PEG-L-asparaginase, Phenylalanine Mustard, Platinol, Platinol-AQ, Prednisolone, Prednisone, Prelone, Procarbazine, PROCRIT, Proleukin, Prolifeprospan 20 with Carmustine implant, Purinethol, Raloxifene, Rheumatrex, Rituxan, Rituximab, Roveron-A (interferon alfa-2a), Rubex, Rubidomycin hydrochloride, Sandostatin, Sandostatin LAR, Sargramostim, Solu-Cortef, Solu-Medrol, STI-571, Streptozocin, Tamoxifen, Targretin, Taxol, Taxotere, Temodar, Temozolomide, Teniposide, TESPA, Thalidomide, Thalomid, Thera-Cys, Thioguanine, Thioguanine Tabloid, Thiophosphoamide, Thioplex, Thiotepa, TICE, Toposar, Topotecan, Toremifene, Trastuzumab, Tretinoin, Trexall, Trisenox, TSPA, VCR, Velban, Velcade, VePesid, Vesanoid, Viadur, Vinblastine, Vinblastine Sulfate, Vincasar Pfs, Vincristine, Vinorelbine, Vinorelbine tartrate, VLB, VP-16, Vumon, Xeloda, Zanosar, Zevalin, Zinecard, Zoladex, Zoledronic acid, Zometa, Gliadel wafer, Glivec, GM-CSF, Goserelin, granulocyte colony stimulating factor, Halotestin, Herceptin, Hexadrol, Hexalen, Hexamethylmelamine, HMM, Hycamtin, Hydrea, Hydrocort Acetate, Hydrocortisone, Hydrocortisone sodium phosphate, Hydrocortisone sodium succinate, Hydrocortone phosphate, Hydroxyurea, Ibritumomab, Ibritumomab Tiuxetan, Idamycin, Idarubicin, Ifex, IFN-alpha, Ifosfamide, IL 2, IL-11, Imatinib mesylate, Imidazole Carboxamide, Interferon alfa, Interferon Alfa-2b (PEG conjugate), Interleukin 2, Interleukin-11, Intron A (interferon alfa-2b), Leucovorin, Leukeran, Leukine, Leuprolide, Leurocristine, Leustatin, Liposomal Ara-C, Liquid Pred, Lomustine, L-PAM, L-Sarcolysin, Meticorten, Mitomycin, Mitomycin-C, Mitoxantrone, M-Prednisol, MTC, MTX, Mustargen, Mustine, Mutamycin, Myleran, Iressa, Irinotecan, Isotretinoin, Kidrolase, Lanacort, L-asparaginase, LCR, FAM-HYD-1, Marizomib (NPI-0052), Lenalidomide, Carfilzomib, Panobinostat, Quisinostat, Selinexor, Oprozomib, and combinations thereof. The anticancer agent can also include biopharmaceuticals such as, for example, antibodies.

Examples of suitable immunotherapeutic agents include, but are not limited to, alemtuzumab, cetuximab (ERBITUX), gemtuzumab, iodine 131 tositumomab, rituximab, trastuzumab (HERCEPTIN), and combinations thereof.

In some examples, the therapeutic agent can comprise an anti-inflammatory agent, such as steroidal and/or non-steroidal anti-inflammatory agents. Examples of steroidal anti-inflammatory agents include, but are not limited to, hydrocortisone, dexamethasone, prednisolone, prednisone, triamcinolone, methylprednisolone, budesonide, betamethasone, cortisone, and deflazacort. Examples of non-steroidal anti-inflammatory drugs include acetaminophen, aspirin, ibuprofen, naproxen, Celebrex, ketoprofen, tolmetin, etodolac, fenoprofen, flurbiprofen, diclofenac, piroxicam, indomethacin, sulindax, meloxicam, nabumetone, oxaprozin, mefenamic acid, and diflunisal.

In some examples, the device is implantable in a subject. In some examples, the device is anatomically designed for the subject. In some examples, the adipose tissue comprises autologous adipose tissue; the second chamber 106 is configured to be connected to a blood vessel of the subject; the third chamber 130, when present, is configured to be connected to a lymphatic vessel the subject; or a combination thereof. For example, the inlet and the outlet of the second chamber 106 can each be independently configured to be connected to an artery or a vein, e.g., using an artery-to-artery or an artery-to-vein anastomosis.

In some examples, the hydrogel matrix 102 is configured to be stable for an amount of time after the device is implanted in the subject. As used herein, "stable" means that 10 wt % or less (e.g., 9% or less, 8% or less, 7% or less, 6% or less, 5% or less, 4% or less, 3% or less, 2% or less, or 1% or less) of the hydrogel matrix 102 biodegrades over the selected time period after the device is implanted in the subject.

In some examples, the hydrogel matrix 102 is configured to be stable for an amount of time of 6 weeks or more after the device is implanted in the subject (e.g., 7 weeks or more, 8 weeks or more, 9 weeks or more, 10 weeks or more, or 11 weeks or more). In some examples, the hydrogel matrix 102 is configured to be stable for an amount of time of 12 weeks or less after the device is implanted in the subject (e.g., 11 weeks or less, 10 weeks or less, 9 weeks or less, 8 weeks or less, or 7 weeks or less). The amount of time for which the hydrogel matrix 102 is configured to be stable can range from any of the minimum values described above to any of the maximum values described above. For example, the hydrogel matrix 102 can be configured to be stable for an amount of time of from 6 weeks to 12 weeks after the device is implanted in the subject (e.g., from 6 weeks to 9 week, from 9 weeks to 12 weeks, from 6 weeks to 8 weeks, from 8 weeks to 10 weeks, from 10 weeks to 12 weeks, from 7 weeks to 12 weeks, from 6 weeks to 11 weeks, from 7 weeks to 11 weeks, or from 7 weeks to 9 weeks).

In some examples, the device is produced by additive manufacturing, such as stereolithography.

In some examples, the device is monolithic.

Figure 10:
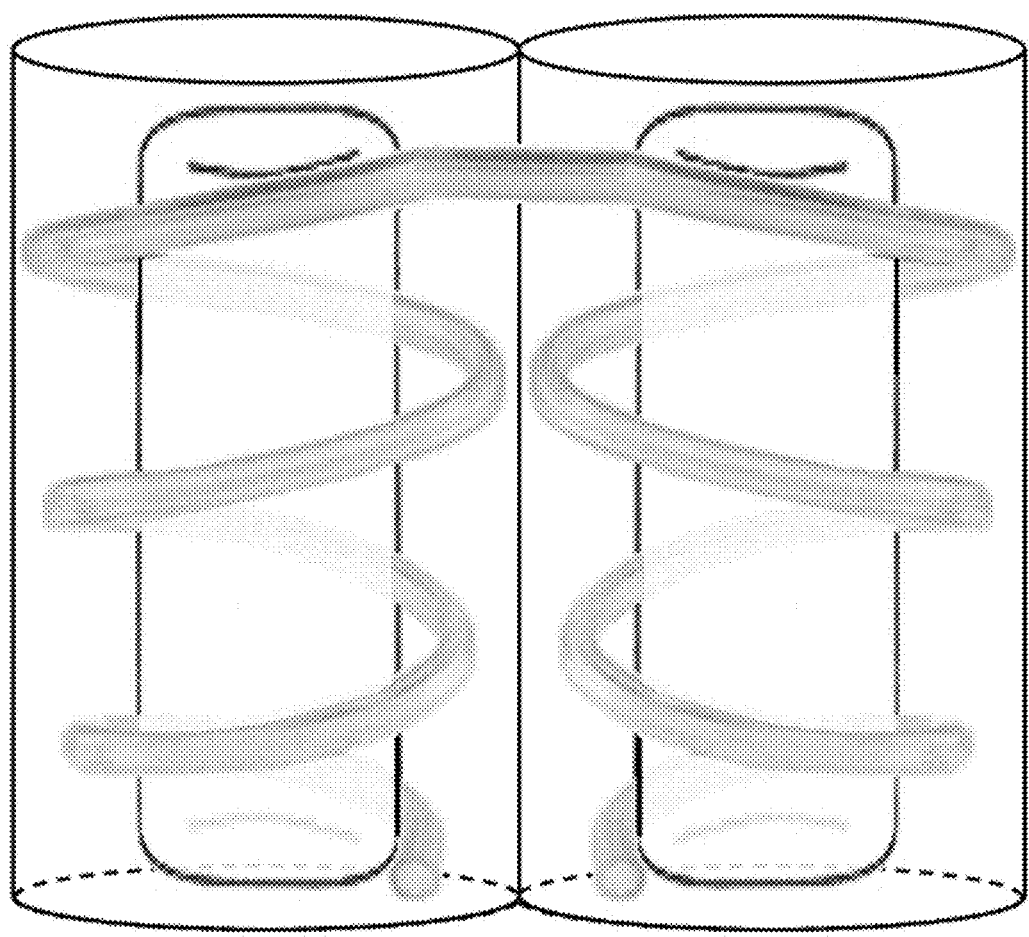
FIG. 10. Schematic view of an example hydrogel device comprising multiple subunits as disclosed herein according to one implementation.
Figure 11:
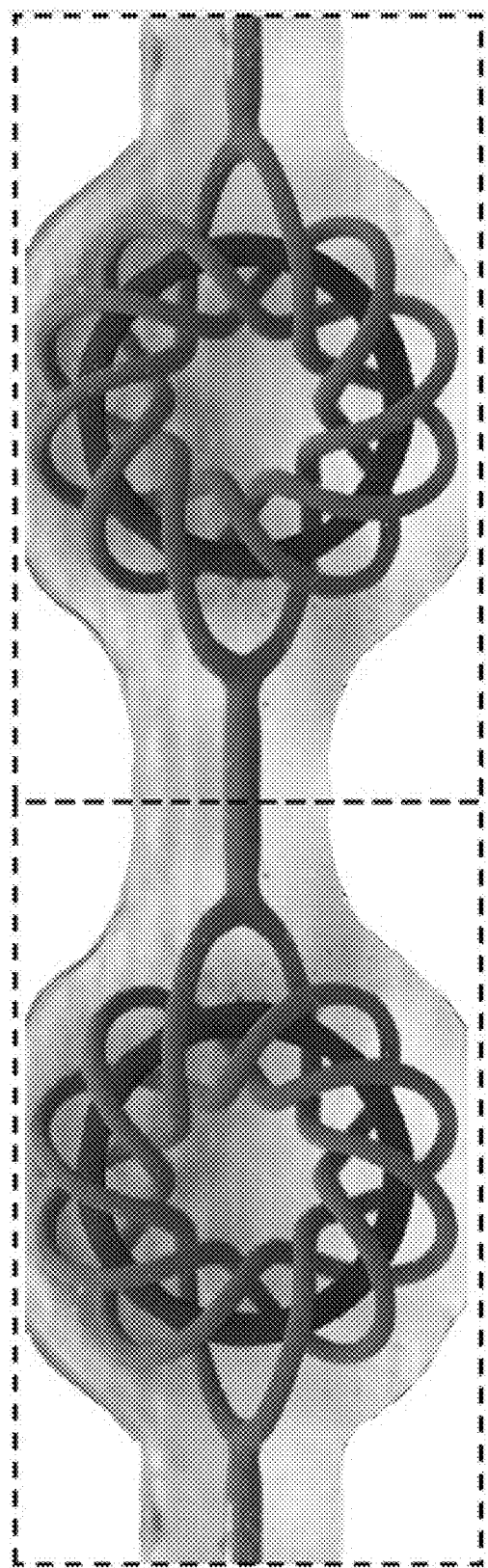
FIG. 11. Schematic view of an example hydrogel device comprising multiple subunits as disclosed herein according to one implementation.
Figure 12:
FIG. 12. Schematic view of an example hydrogel device comprising multiple subunits as disclosed herein according to one implementation.

Also disclosed herein are devices comprising multiple joined subunits, wherein each subunit of the device comprises: a continuous hydrogel matrix; a first chamber in the hydrogel matrix; and a second chamber in the hydrogel matrix; wherein the first chamber and the second chamber are each independently perfusable; wherein the first chamber is fluidly independent from the second chamber; wherein the first chamber is configured to be at least partially filled with adipose tissue; wherein the second chamber is configured to be at least partially filled with an oxygenated fluid; wherein the first chamber is defined by a first border; wherein the second chamber is defined by a second border; and wherein the first chamber and the second chamber are spaced apart from each other by an average distance of from 50 micrometers (microns, μm) to 800 μm as measured from the first border to the second border. Example devices comprising multiple joined subunits are shown in FIG. 10-FIG. 12.

Also disclosed herein are devices comprising multiple joined subunits, wherein each subunit comprises: a continuous hydrogel matrix; and one or more chambers (e.g., 2 or more, 3 or more, 4 or more, 5 or more, 6 or more, 7 or more, 8 or more, 9 or more, or 10 or more) in the continuous hydrogel matrix; wherein each of the one or more chambers in each subunit is fluidly independent from one another; such that, when multiple subunits are joined together, the device comprises: a continuous hydrogel matrix; a first chamber in the hydrogel matrix; and a second chamber in the hydrogel matrix; wherein the first chamber and the second chamber are each independently perfusable; wherein the first chamber is fluidly independent from the second chamber; wherein the first chamber is configured to be at least partially filled with adipose tissue; wherein the second chamber is configured to be at least partially filled with an oxygenated fluid; wherein the first chamber is defined by a first border; wherein the second chamber is defined by a second border; and wherein the first chamber and the second chamber are spaced apart from each other by an average distance of from 50 micrometers (microns, μm) to 800 μm as measured from the first border to the second border. In some examples, when multiple subunits are joined together, the device further comprises a third chamber in the hydrogel matrix, wherein the third chamber is perfusable and fluidly independent from the first chamber and the second chamber.

In some examples, the number of chambers can independently vary for each of the multiple subunits. In some examples, each of the multiple subunits has the same number of chambers.

In some examples, the average characteristic dimension of each of the one or more chambers can vary independently within and/or between each of the multiple subunits.

In some examples, the composition of the hydrogel matrix can independently vary within and/or between each of the multiple subunits. In some examples, the device further comprises a therapeutic agent dispersed within the hydrogel matrix. In some examples, the presence, the absence, the concentration, the identity, or a combination thereof of the therapeutic agent can independently vary within and/or between each of the multiple subunits.

In some examples, the plurality of zeolite nanotubes can comprise a mixture of a plurality of populations of subunits, wherein each population of subunits within the mixture has a different hydrogel matrix composition, number of chambers, average characteristic dimension for the chambers, or combination thereof.

Methods

Also disclosed herein are methods of manufacturing any of the devices disclosed herein. For example, the methods can comprise making the device using additive manufacturing. In some examples, the additive manufacturing comprises stereolithography.

In some examples, the method comprises making the device based on a 3D model. In some examples, the method further comprises using a fractal space-filling model to computationally derive the 3D model.

In some examples, the first chamber, the second chamber, the third chamber (when present), or a combination thereof, can each independently be formed from a model based on a tessellation of polyhedrons. For example, the first chamber, the second chamber, the third chamber (when present), or a combination thereof can each independently be formed from a computational 3D space-filling model. For example, the second chamber and/or the third chamber (when present) can each independently be formed from a computational 3D space-filling model to maximize the surface area while minimizing flow resistance and providing for robust mass transport. The computational 3D space-filling model can, for example, be a fractal space-filling model.

In some examples, the 3D model is based on an anatomical image of a subject. In some examples, the method further comprises collecting the anatomical image of the subject.

In some examples, the method further comprises providing a pre-polymerization solution for the additive manufacturing.

In some examples, the pre-polymerization solution comprises the photosensitive polymer. The pre-polymerization solution can, for example, comprise the photosensitive polymer in an amount of 5 wt % or more (e.g., 6 wt % or more, 7 wt % or more, 8 wt % or more, 9 wt % or more, 10 wt % or more, 11 wt % or more, 12 wt % or more, 13 wt % or more, 14 wt % or more, 15 wt % or more, 16 wt % or more, 17 wt % or more, 18 wt % or more, 19 wt % or more, 20 wt % or more, 21 wt % or more, 22 wt % or more, 23 wt % or more, 24 wt % or more, 25 wt % or more, 26 wt % or more, 27 wt % or more, 28 wt % or more, or 29 wt % or more). In some examples, the pre-polymerization solution can comprise the photosensitive polymer in an amount of 30 wt % or less (e.g., 29 wt % or less, 28 wt % or less, 27 wt % or less, 26 wt % or less, 25 wt % or less, 24 wt % or less, 23 wt % or less, 22 wt % or less, 21 wt % or less, 20 wt % or less, 19 wt % or less, 18 wt % or less, 17 wt % or less, 16 wt % or less, 15 wt % or less, 14 wt % or less, 13 wt % or less, 12 wt % or less, 11 wt % or less, 10 wt % or less, 9 wt % or less, 8 wt % or less, 7 wt % or less, or 6 wt % or less). The amount of photosensitive polymer in the pre-polymerization solution can range from any of the minimum values described above to any of the maximum values described above. For example, the pre-polymerization solution can comprise the photosensitive polymer in an amount of from 5 wt % to 30 wt % (e.g., from 5 wt % to 17 wt %, from 17 wt % to 30 wt %, from 5 wt % to 10 wt %, from 10 wt % to 15 wt %, from 15 wt % to 20 wt %, from 20 wt % to 25 wt %, from 25 wt % to 30 wt %, from 5 wt % to 25 wt %, from 10 wt % to 30 wt %, from 10 wt % to 25 wt %, from 15 wt % to 25 wt %, or from 18 wt % to 22 wt %).

In some examples, the pre-polymerization solution further comprises a solvent. Any suitable solvent can be used. The solvent can, for example, comprise tetrahydrofuran (THF), N-methyl-2-pyrrolidone (NMP), dimethylformamide (DMF), N-methylformamide, formamide, dichloromethane ($CH_2Cl_2$), ethylene glycol, polyethylene glycol, glycerol, alkane diol, ethanol, methanol, propanol, isopropanol, water, acetonitrile, chloroform, toluene, methyl acetate, ethyl acetate, acetone, hexane, heptane, tetraglyme, propylene carbonate, diglyme, dimethyl sulfoxide (DMSO), dimethoxyethane, xylene, dimethylacetamide, methylene chloride, hexafluoro-2-propanol, or combinations thereof. In some examples, solvent comprises water.

In some examples, the pre-polymerization solution further comprises the photoabsorber. In some examples, the pre-polymerization solution further comprises the therapeutic agent.

In some examples, method further comprises lining the second chamber with the plurality of cells.

In some examples, the method further comprises at least partially removing or degrading the photoabsorber prior to implanting the device. For example, at least 70% (e.g., at least 75%, at least 80%, at least 85%, at least 90%, at least 95%, or at least 99%) of the photoabsorber can be removed or degraded prior to implanting the device.

In some examples, the photoabsorber is at least partially washed out of the device. In some examples, the photoabsorber is degradable independent of any degradation of the hydrogel matrix. In some examples, the photoabsorber is degradable by chemical or physical processes. For example, the photoabsorber can be photobleachable by exposure to absorbable light having a wavelength 365-450 nm wavelength, chemical degradation such as by peroxides, or any other suitable material, or removable by exposure to boiling aqueous solution, such as water, or any other suitable material.

Also disclosed herein are methods of treating a subject in need thereof, the methods comprising implanting the device into the subject.

In some examples, the first chamber of the implanted device is at least partially filled with adipose tissue, such as autologous adipose tissue. In some examples, the first chamber of the implanted device is at least partially filled with a mixture comprising adipose tissue. The mixture can, for example, further comprise an additional component, which can, for example, improve the uptake of the fat by the subject. For example, the additional component can comprise platelets, plasma, platelet-rich plasma (PRP), stem cells, a protein, or a combination thereof.

In some examples, the device is implanted into a breast of the subject. For example, the method can comprise breast reconstruction or augmentation.

In some examples, the method further comprises connecting the second chamber to a blood vessel of the subject. For example, the method can comprise connecting the second chamber to an artery and/or a vein. In some examples, the method can comprise connecting the second chamber using an artery-to-artery or an artery-to-vein anastomosis.

In some examples, the method comprises independently connecting the inlet and the outlet to a blood vessel of the subject. For example, the method can comprise independently connecting the inlet and the outlet of the second chamber to an artery or a vein. In some examples, the method can comprise connecting the inlet and/or the outlet of the second chamber using an artery-to-artery or an artery-to-vein anastomosis.

In some examples, the method further comprises connecting the third chamber (when present) to a lymphatic vessel of the subject. In some examples, method comprises independently connecting the inlet and the outlet of the third chamber (when present) to a lymphatic vessel of the subject.

In some examples, the method further comprises anatomically designing the device for the subject.

In some examples, the methods can comprise breast reconstruction and treatment of an oncological disorder, such as breast cancer. In some examples, the devices can further include a therapeutic agent, for example for treatment of the oncological disorder.

For the treatment of oncological disorders, the devices disclosed herein can be administered to a patient in need of treatment in combination with other antitumor or anti-cancer substances and/or with radiation and/or photodynamic therapy and/or with surgical treatment to remove a tumor. These other substances or treatments can be given at the same as or at different times from the devices disclosed herein. For example, the devices disclosed herein can be used in combination with mitotic inhibitors such as taxol or vinblastine, alkylating agents such as cyclophosphamide or ifosfamide, antimetabolites such as 5-fluorouracil or hydroxyurea, DNA intercalators such as adriamycin or bleomycin, topoisomerase inhibitors such as etoposide or camptothecin, antiangiogenic agents such as angiostatin, antiestrogens such as tamoxifen, and/or other anti-cancer drugs or antibodies, such as, for example, GLEEVEC (Novartis Pharmaceuticals Corporation) and HERCEPTIN (Genentech, Inc.), respectively, or an immunotherapeutic such as ipilimumab and bortezomib.

A number of embodiments of the invention have been described. Nevertheless, it will be understood that various modifications may be made without departing from the spirit and scope of the invention. Accordingly, other embodiments are within the scope of the following claims.

The examples below are intended to further illustrate certain aspects of the systems and methods described herein and are not intended to limit the scope of the claims.

EXAMPLES

The following examples are set forth below to illustrate the methods and results according to the disclosed subject matter. These examples are not intended to be inclusive of all aspects of the subject matter disclosed herein, but rather to illustrate representative methods and results. These examples are not intended to exclude equivalents and variations of the present invention, which are apparent to one skilled in the art.

Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of measurement conditions, e.g., component concentrations, temperatures, pressures and other measurement ranges and conditions that can be used to optimize the described process.

Example 1—Development of the Neobreast: A 3D Printed Vascularized Adipose Gland for Breast Reconstruction Breast reconstruction has improved over the years, and the two main options are implant-based reconstruction and autologous reconstruction. Autologous breast reconstruction has evolved dramatically; initially, it was intended to only recreate an absent breast. Later, the surgical technique was refined to provide a more aesthetic and natural appearance by improving the mastectomy techniques to restore the patient's skin envelope and nipple-areola complex resulting in a more natural appearance; these improvements resulted in significantly increased patient satisfaction and improved quality of life. Currently, with the advent of more precise microsurgical techniques, some functionality is given to the reconstructed breast, by including nerves to provide sensation to the skin and nipple-areola complex, the patient's quality of life is improved even more.

Alloplastic, or implant-based, breast reconstruction has improved but is still problematic due to the limitations of the prosthesis. In order to improve coverage over the implant, fat grafting has been developed, but is limited by the lack of blood supply proximity. The advent of 3D-printing technology has facilitated the ability to print implants with improved materials that are more customized to the patient, however, this is still limited due to the synthetic nature of this option.

If a network of blood vessels could be 3D-printed and surgically connected to the patient vasculature, surgeons could ensure the autologous fat transplanted from the patient is adequately vascularized, creating a fat gland organ, termed Neobreast, which would be made of natural tissue but not require a large donor site. For this project, the creation of a 3D-printed, dual vessel construct, the Neobreast, is proposed. Two channels can run through the Neobreast; the first channel can allow blood flow through the Neobreast and the second channel can house transplanted fat cells. This can ensure that the fat surround is kept within a specific distance of the artificial vasculature, allowing blood and oxygen supplies to the transplanted tissues. The reconstructive journey of the patient can be shortened with this design, allowing them to return to their lives soon after mastectomy, enabling a faster return to their quality of life. In addition to testing the viability of the Neobreast as a vascularized breast organ, it can also be tested as a housing for a breast cancer nanovaccine which has the potential of diminishing and/or eliminating breast cancer recurrence in this patient population.

The goal is to have a network of blood vessels 3D-printed and surgically connected to the patient's vasculature. Surgeons can then ensure the fat transplant is adequately vascularized, allowing the best possible outcome for patients.

There is 3D-printing technology employing stereolithography that can generate exceptionally complex and scalable vascular networks that can engraft in vivo and support the function of embedded parenchymal cells (Grigorian et al. Science (80-). 2019, doi:10.1126/science.aav9750). Stereolithographic 3D-printing uses a photoactive water-based and protein-containing solution that can be crosslinked into a hydrogel through photopolymerization, with a pixel resolution down to 10 μm to construct vessel structures as small as 300 μm in diameter, precisely the target range for this work. This research also demonstrated that two non-intersecting vessel systems could be created (FIG. 1). The conformation of these vessels can be varied, providing an inter-vessel distance of 300 μm, which is a distance suitable for a vascular network to provide nutrients and oxygen to a payload of fat transplant injected into the secondary network. This procedure can be optimized to create multiple fluidic vessels that more closely mimics the architecture of human tissue and thereby uniquely provides a route towards the generation of a vascularized autologous fat implant of arbitrary size and shape to meet the patient's needs.

For this project, the creation of a 3D-printed, dual vessel construct, termed the Neobreast is proposed. The first channel can be connected into the vasculature (described in detail in the research strategy below) allowing blood flow through the Neobreast. The second channel can be significantly larger and can be filled with transplanted fat cells. This can ensure that the fat surround is kept within a specific distance of the artificial vasculature, ensuring blood and oxygen supplies to the transplanted tissues. Prior data suggests that the hydrogel framework is bio-stable for up to eight weeks, allowing time for vascularization by the host system.

The Neobreast advances reconstructive technology, improving psychological and quality of life outcomes for breast cancer survivors. It is hypothesized that a well-vascularized 3D-printed bio-structure (Neobreast) can have an adequate environment for adipose tissue to survive.

Aim 1, will demonstrate integration of the Neobreast with host vasculature and improved transplant outcomes in small and large animal models. It is hypothesized that the Neobreast architecture will successfully integrate into the host vasculature, increasing the viability of the transplanted fat cells. In order to test this hypothesis, two sub aims are devised. Sub-aim 1.1, will test Neobreast configurations to determine the optimal formation for integration into a mouse and rabbit model. Within this aim, the ideal shape of the printed vasculature to consistently integrate into the host can be identified. Microsurgical techniques utilizing custom-designed couplers can ensure consistent surgical implantation. Sub aim 1.2, will test Neobreast configurations to optimize transplanted tissue viability. Within this aim, the ideal distance between the fat channels and vasculature channels to ensure the viability of the fat can be identified. Fat viability can be compared to a non-vascularized transplant of equal volume. During this aim, data will be gathered regarding manufacturing processes and material chemistry.

At the conclusion of this project, a fully optimized Neobreast ready to enter the regulatory process for clinical usage will be developed. A patient-focused approach can be maintained throughout the regulatory process and development. This project can be the transformative step in using 3D-printed vasculature for organ transplants.

The research strategy is detailed as follows:

Aim 1, will demonstrate integration of the Neobreast with host vasculature and improved transplant outcomes in small and large animal models. While the capability to create a non-intersecting, dual printed channels that can integrate into host vasculature has been demonstrated, it will be validated that this technology works with a fat-loaded channel in the secondary compartment to validate its efficacy for delivery of oxygen and nutrients using the primary vascular channel to the second fat channel. Different Neobreast vascular network topologies can be screened to identify optimal architectures that can successfully integrate into the host vasculature and thereby increase the viability of the transplanted fat cells.

In subaim 1.1, Neobreast configurations can be tested to optimize transplanted tissue viability. Hydrogels can be fabricated by stereolithography and can be assessed for vascular efficiency using perfusion tissue culture and human cells transduced with molecular imaging readouts. Briefly, engineered tissues containing luciferase-expressing (Luc2P) HEK cells at 5-50e6 cells/mL within a bulk 20 wt % PEGDA 6 kDa hydrogel can be fabricated. Luciferin substrate will be perfused and luminescence of the hydrogel as a function of vascular architecture over 2 hours can be quantified. Preliminary data on the effect of cell density in hydrogels, as well as the ability to screen algorithmic vascular topologies for luminescence with this assay has been demonstrated. Importantly, the total vascular volume of the hydrogel can be held constant (50 μL in a 1 mL hydrogel) across all topologies, such that the total luminescence can provide a direct comparison between the efficiency across networks. Corresponding experiments in gels without cells can be conducted, where wall displacement and fluid velocity can be measured via particle image velocimetry (PIV). To map the diffusive transport, the diffusion of fluorescently labeled dextran can be quantified from the vascular lumen into the interstitial zone.

Subaim 1.2, can test Neobreast configurations to determine the optimal formulation for integration into a mouse and rabbit model. The ideal distance between the fat channels and vascular channels in the 0.3 mm-1 mm range to ensure the viability of the fat can be identified. Based on the nature of fat cells, it is believed that the fat channel will need to be significantly larger than the artificially printed blood vessels; fat channels that are 300 μm, 500 μm, and 1 mm in diameter can be tested. Architectural blueprints for the vascular networks can be grown computationally that can maximize surface area of the vasculature while minimizing flow resistance and providing for robust mass transport and thus fat tissue survival (Grigoryan B et al. Science (80-). 2019, doi:10.1126/science.aav9750). These vascular constructs can then be implanted, for example, by a microvascular surgery team.

The surgery can be performed in alignment with all regulatory protocols to ensure the justification for the use of research animals involved and for their safety. In order to reduce the needed number of animals for these studies, these aims have been designed to be conducted on the same cohort of rabbits, decreasing the time to the proposed outcomes. The primary outcomes measured in this aim will be fat viability and vascular integration. Histology studies can be used to image transplanted tissue for necrosis, apoptosis, and vascular invasion. Necrosis can be measured by using antibodies against Heat Shock Protein 90 and Histone H1 Complex. Apoptosis can be assessed by using antibodies against caspase 9 and cytochrome c. The goal of these studies is not to differentiate between apoptosis and necrosis, but to provide a full picture of cell death. To measure neovascularization of the transplanted tissue, immunohistochemistry with *Griffonia simplicifolia* Lectin (Liang et. al. Int J Ophthalmol. 2012. doi:10.3980/j.issn.2222-3959.2012.01.01), and confocal microscopy of dual-labeled lectins can be used (Baranski et al. Proc Natl Acad Sci USA. 2013. doi:10.1073/pnas.1217796110). Should staining methods produce mixed or unclear results, flow cytometry can be utilized. After Aim 1, a functional model of the neobreast can be obtained that allows increased viability of transplanted fat cells and that could be vascularized by the host organism (FIG. 3-FIG. 8).

Milestones: Aim 1 can demonstrate an improved construct for breast reconstruction. (1.) Demonstrate that the Neobreast can allow for increased viability of transplanted fat cells. (2.) Prove that the Neobreast can be vascularized by the host organism.

Impact: These studies can allow for significant improvement of breast reconstruction in mastectomy patients. These experiments can be conducted in a large animal model, meaning there will be significant support for immediate translation of this work into clinical studies, keeping in line with the BCRP goals of getting improved treatments to breast cancer patients faster.

Microsurgical connection of Neobreast: The 3D printed developed breast can be connected to the superficial inferior epigastric artery (SIEA). The anatomy was outlined by Giessler et al., where they described the design of the SIEA fascia flap in a rabbit model (Giessler G A et al. Microsurgery. 2007. doi:10.1002/micr.20413). A 1-mm Synovis® artery coupler can be used to perform the microsurgical connection between the 3D-printed blood vessel and the superficial inferior epigastric artery. This procedure can be performed on a total of 15 rabbits.

Figure 9:
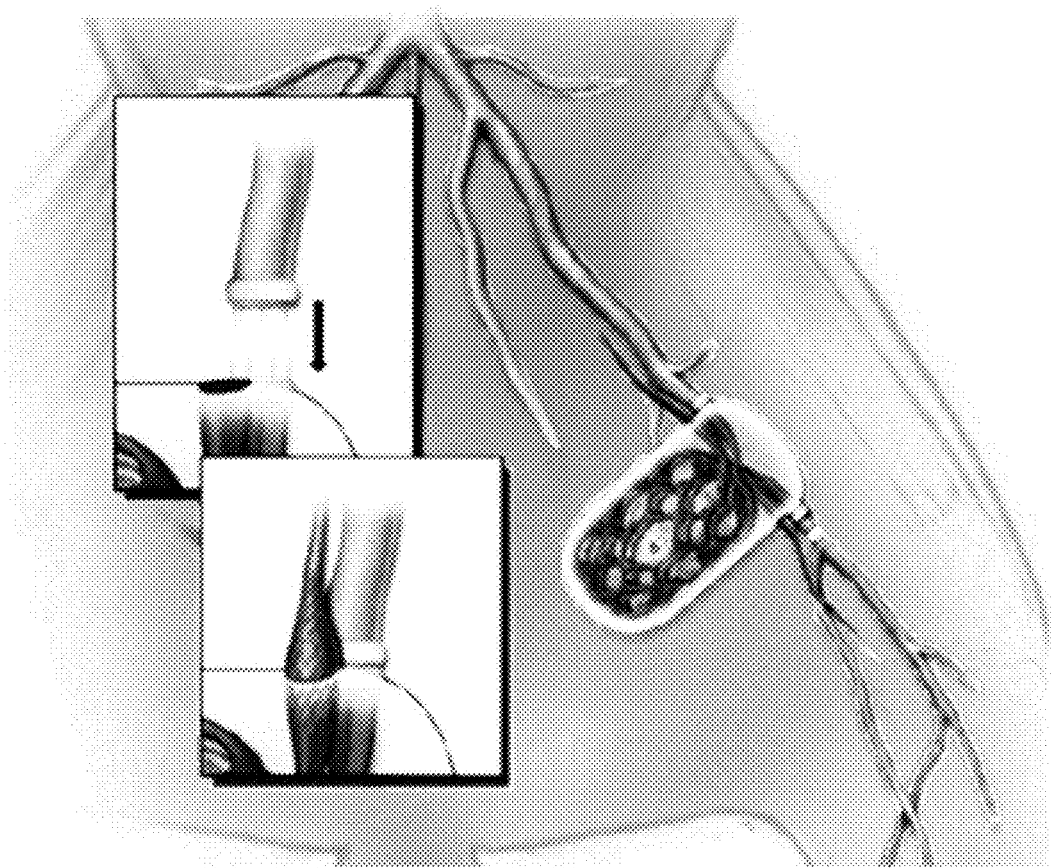
FIG. 9. Neobreast model connected to the femoral artery of a rabbit model.

Alternative microsurgical connection: If there are issues with the microsurgical connection, as an alternative, instead of using the SIEA vessel, the femoral artery can be used as the main vessel where the neobreast can be connected. As demonstrated in a rat model by Zhang et al., previously 3D-printed blood vessels models (AngioChips) can be anastomosed to the femoral artery using an artery-to-artery or an artery-to-vein anastomosis (FIG. 9) (Zhang B et al. Nat Mater. 2016. doi:10.1038/nmat4570).

Beyond cancer reconstruction, this technology has potential in many spaces. The Neobreast can prove a technology of pre-vascularizing a transplanted organ, in this case, fat. Success with the Neobreast can provide an avenue of research into similar research studies implanting other organs and tissues.

Example 2

Breast cancer is a multifaceted disease. The treatment of which goes far beyond the initial declaration of "Cancer-Free." Forty percent (40%)*of breast cancer patients have a mastectomy or lumpectomy as part of their cancer treatment. These women often experience significant anxiety and depression regarding their mastectomy. The mental distress is long-lasting, with persistent levels of anxiety and stress fifteen months post-mastectomy*, which significantly compromises the quality of life for survivors (*Statistics and some content about anxiety and depression in breast cancer survivors in this section were informed by: Farooqi Y N. Depression and anxiety in mastectomy cases. Illn Cris Loss. 2005. doi:10.1177/105413730501300306). Body image, psychosocial and sexual conflicts* can arise around the loss of one or both breasts. Breast reconstruction can reduce anxiety and depression in these patients, with immediate reconstruction having significant benefits even when compared to delayed reconstruction. However, even immediate reconstruction does not eliminate the risk of anxiety and depression. Reconstruction, as it stands, is an imperfect science. Breast symmetry is a primary concern, but with one of the two major reconstruction methods, breast implants, the implants are limited in their ability to achieve a perfectly symmetrical appearance. This makes current implant technology undesirable.

With current technologies and techniques needing improvement, new methods of reconstruction are necessary. The Neobreast can be that solution for breast reconstruction patients. One reason it is considered an advancement on current technology is that it would not be limited to pre-defined, fabricated shapes and sizes intended to fit all women.

Autologous tissue reconstruction is another current tool surgeons use in breast reconstruction. Unlike implants, reconstruction utilizing autologous tissue results in a reconstructed breast that follows changes in body dynamics, like weight gain, and patients have higher satisfaction rates. The Neobreast can improve upon autologous grafting for reconstruction by providing a vascularized scaffold for the fat, improving the efficacy of the transplant. Vascularizing the tissue provides a significant advantage and expands access to this method of reconstruction.

Cancer survivors do not stop being patients as soon as they are cancer-free; reconstructive care improves the quality of life and reduces symptoms of mental distress in cancer survivors. This aspect of care is continually underserved, and the Neobreast creates significant benefits in this space.

Beyond cancer reconstruction, this technology has potential in other spaces as well. The Neobreast will prove a novel technology of pre-vascularizing a transplanted organ, in this case, fat. Success with the Neobreast can provide an avenue for research into similar research studies implanting other organs and tissues. The Neobreast can move breast cancer therapy forward. It addresses significant challenges by providing a less invasive, less toxic reconstructive treatment that can significantly impact breast cancer reconstructive success.

Right now, it is possible to do fat grafting, but it is limited by the blood supply. This construct will allow a viable breast, anatomically designed for the patient, to be built, which has variable weight for the patient and has a blood supply. This would effectively eliminate the need for traditional breast implants in post-breast cancer reconstructive surgeries. This, in conjunction with the clear benefits of improving reconstructive therapy, make the Neobreast a leap forward in the care of breast cancer patients.

This research will begin by working in the pre-clinical phase of research with the Neobreast. The research will involve large animal work and, once viability is proven, the plan is to move forward with human trials. The research will allow for significant improvement of breast reconstruction in mastectomy patients. Experiments will be conducted in large animal models, meaning significant support for immediate translation into clinical studies, while supporting the Breast Cancer Research Program goal of getting improved treatments to breast cancer patients faster. This work merges two technologies: microsurgery & 3D-printing an organ. As this is the first time this has been done, this technology can become a stepping point for other transplanted organs with heightened metabolic loads.

It is hypothesized that a well-vascularized 3D-printed bio-structure (Neobreast) will have an adequate environment for adipose tissue to survive, and that the Neobreast architecture will successfully integrate into the host vasculature, increasing the viability of the transplanted fat cells. These hypotheses will be tested using Aim 1, sub-aims 1.1 and 1.2. Aim 1, will demonstrate integration of the Neobreast with host vasculature and improved transplant outcomes in small and large animal models. Sub-aim 1.1: a) will test the Neobreast construct to optimize formation integration in mice & rabbit models, b) identify the ideal shape of printed vasculature to integrate into the host, and c) microsurgical methods using custom couplers will ensure consistent implantation. Sub-aim 1.2 a) will test the Neobreast construct to optimize transplanted tissue viability, b) identify the ideal distance between fat & vasculature channels to ensure fat viability, and c) compare fat viability to an equal volume, non-vascularized transplant.

The 3D-printed artificial, biocompatible vasculature surrounded by transplanted fat can serve as a viable surgical implant during the reconstructive process. Expert microvasculature surgery techniques can be employed to reconnect these artificial vessels, allowing much larger fat transplants; resulting in a single surgery for cancer patients. Reconstructive surgery can be improved with this breast organ technology; leading to the creation of more complex organs. After proving the viability of the Neobreast as a vascularized breast organ, it will then be tested as a housing for a breast cancer nanovaccine.

The Neobreast advances reconstructive technology, improving psychological and quality of life outcomes for breast cancer survivors, while the potential for a therapeutic arm prevents further disease. Additionally, the Neobreast makes improvements over existing technology and lessens limitations in the field of breast cancer reconstruction by improving the: 1) existing technology of implant-based breast reconstruction post-mastectomy and 2) surgical technique of autologous transplantation.

Beyond cancer reconstruction, this technology has potential in many spaces. The Neobreast can demonstrate pre-vascularizing a transplanted organ, in this case, fat. Success with the Neobreast can provide an avenue of research into similar research studies implanting and vascularizing other organs and tissues. The aforementioned therapeutic arm of Neobreast, can house immunotherapy that prevents recurring breast cancer and has the potential of being administered during the reconstructive process.

It is important to emphasize that this concept combines three realms: (a) microsurgery, (b) the ability to vascularize, or bring blood supply to tissue, and (c) 3D-printing. Developing microvascular channels allows the fat to proliferate and not reabsorb. The plan is to take the 3-dimensional scaffolding, build an organ, and vascularize it by connecting it to the body. As this is the first time this has been done, the potential for this technology to be a stepping point for other transplanted organs with heightened metabolic loads is great.

Example 3

Herein, it is further proposed to augment the Neobreast with embedded NanoVax in the bulk of the hydrogel, to construct a dual-use implant leading to a breakthrough in patient quality of life and disease remission. This design can effectively prevent breast cancer recurrence and metastases while allowing breast cancer survivors to return to their lives soon after mastectomy.

The therapeutic Neobreast addresses two primary challenges in breast cancer therapy by: 1) significantly reducing the mortality associated with metastatic, recurring breast cancer, and 2) creating an immunotherapy-based treatment with greater efficacy and reduced mortality. The Neobreast can create an immunotherapy that prevents recurring breast cancer administered during the reconstructive process. By incorporating the therapeutic DC-Nanovax into the gel matrix used to create the vasculature, the need for additional treatments can be eliminated, allowing patients to focus on healing and returning to their life before cancer. The Neobreast advances reconstructive technology, improving psychological and quality of life outcomes for breast cancer survivors, while the therapeutic arm prevents further disease. It is hypothesized that a well-vascularized 3D printed bio-structure (Neobreast) will have an adequate environment for adipose tissue to survive and serve as an immune organ to expand the immune response to the nano-vaccine, significantly reducing the rate of breast cancer recurrence and distant metastases.

Example 4

The Neobreast is a fat gland organ containing a network of 3D-printed vessels to ensure the viability of autologous fat transplants for breast reconstruction. The 3D-printed vessels will contain at least 2 different channels (potentially 3) depending on the needs of the tissue. The first channel will be connected to the vasculature allowing blood to flow through the fat gland organ. The second channel will be significantly larger and will be filled with transplanted fat cells. The space and orientation of the 3D-printed vessels can ensure that the fat surround is receiving adequate blood and oxygen to maintain viability and promote adequate vascularization. The optional third channel is a lymphatic channel to allow for the removal of waste, toxins or unwanted materials. This channel can become particularly relevant if the Neobreast is to be used as a therapeutic fat gland (i.e., a fat gland which contains an anti-cancer agent such as the nanovax to prevent cancer recurrence).

3D-printing technology employing stereolithography can generate exceptionally complex and scalable vascular networks that can be engrafted in vivo and support the function of embedded parenchymal cells. Stereolithographic 3D-printing uses a photoactive water-based and protein containing, solution that can be crosslinked into a hydrogel through photopolymerization, with a pixel resolution down to 10 µm to construct vessel structures as small as 300 µm in diameter, precisely the target range needed for this work. Prior data suggest that this hydrogel framework is bio-stable for up to eight weeks, at which point the channels would be bioabsorbed. It is hypothesized that this will be a sufficient amount of time for vascularization by the host system, thus these 3D-printed vessels would simply be used to provide blood and oxygen supplies to the autologous fat graft until the graft is able to be self-sufficient. The 3D-printed vessels will be connected to either the superficial inferior epigastric artery (SIEA) using a 1-mm Synovis® artery coupler or the femoral artery using an artery-to-artery or an artery-to-vein anastomosis. After proving viability of the Neobreast as a vascularized fat gland organ for breast reconstruction, it will also be tested as a housing for a breast cancer nanovaccine. The nanovaccine will be embedded in the bulk of the hydrogel framework to construct a dual-use function (reconstruction and therapeutic).

The Neobreast will shorten the reconstructive journey of the patient, allowing them to return to their lives soon after mastectomy, enabling a faster return to their quality of life. The therapeutic Neobreast design has the added potential of diminishing breast cancer recurrence in survivors. Beyond cancer reconstruction, this technology has potential in many other spaces. The Neobreast will pre-vascularize a transplanted organ, in this case, fat. As a result, success with the Neobreast will provide an avenue of research into similar research studies implanting other organs and tissues.

Example 5

Breast Cancer is the second most common cancer diagnosed in American women (Siegel R L. Cancer Statistics. *CA Cancer J Clin.* 2019). Throughout her lifetime, a woman has a 1 in 8 chance of developing breast cancer, with over 300,000 cases of breast cancer diagnosed each year. Death from breast cancer is declining in early-stage breast cancer patients thanks to surgery and introduction of hormone therapy, but more than 40,000 women still die of the disease each year (Breastcancer.org. US Breast Cancer Statistics. US Breast Cancer Statistics. https://www.breastcancer.org/symptoms/understand_bc/statistics. Published 2019. Accessed Oct. 3, 2019). Although recent advances in cancer immunotherapy have raised the hope for complete cure of human cancers, only a small percentage of patients with selected cancer types, such as melanoma, non-small-cell lung cancer and colorectal cancer with microsatellite instability, have benefited from these treatments (Kalyan A et al. *J Gastrointest Oncol.* 2018. doi:10.21037/jgo.2018.01.17). Response rate is very low in the immunologically "cold" tumors (i.e., non-inflamed), including breast cancer. More effective and innovative treatment options are urgently needed to prevent tumor recurrence and metastasis and to fight against late-stage diseases. Herein, a dual-use vascularized implant that can deploy cancer vaccines in the patient and simultaneously aid in volumetric reconstructive surgery for dramatically improved clinical outcomes is described.

Breast Cancer Vaccine Development. Therapeutic cancer vaccine provides an alternative approach to treating human cancers. Both peptide vaccines and mRNA vaccines (packaged in various nanoparticle forms) have been evaluated in clinical trials as single agents, and partial and complete responses have been observed. A nanotechnology-based platform to develop potent cancer vaccines (NanoVax) has been designed. It comprises porous silicon microparticles that are loaded with tumor antigen peptides. The vaccine particles are effectively taken up by dendritic cells (DCs, the most effective antigen-presenting cells inside the body). The platform allows robust DC stimulation as indicated by changes in cell morphology and high expression levels of interferon-b and its downstream Rantes (CCL-5). The NanoVax was applied to treat mice with primary Her2-positive breast tumors, and excellent therapeutic efficacy was demonstrated. In addition, approaches to further improve vaccine efficacy have been identified. For example, the antigen peptide was co-packaged with soluble adjuvants and incomplete inhibition of primary tumor growth in a murine model of Her2-positive breast cancer was demonstrated. These studies can provide the basis for the development of therapeutic cancer vaccines to treat any subtype of breast cancer. Successful translation of a therapeutic cancer vaccine into a treatment for patients will have a huge impact on the medical community and pharmaceutical industry. It will benefit HER2 positive breast cancer patients who have failed current treatment due to therapy resistance.

NanoVax differs from other cancer vaccines in that the PSM particle (porous silicon microparticle) serves both as an adjuvant to stimulate antigen-presenting cell maturation and maintain their activity and as a reservoir for sustained release of tumor antigens and soluble adjuvants. Particulate adjuvants such as aluminum oxide (alum) and nanoformulations have been applied as adjuvants for vaccine development. However, most of these particulate adjuvants are not suitable for a therapeutic cancer vaccine, as they are unable to trigger stimulation of cytotoxic T cells. In contrast, PSM mediates stimulation of type I interferon signaling, and soluble adjuvants loaded inside PSM further boost this activity.

It is believed that if deployed properly, this vaccine can prevent breast cancer recurrence in breast cancer patients, reducing mortality and improving quality of life.

Breast Reconstruction. After a mastectomy, approximately 60% of women undergo breast reconstruction. In 2018 alone, 101,657 women underwent this surgical procedure, representing a 29% increase in breast reconstruction rates from 2000 to 2018 (American Society of Plastic Surgeons (ASPS). 2018 *Plastic Surgery Statistics Report.;* 2018). This trend is likely representative of clinicians considering reconstruction a crucial part of breast cancer recovery.

Currently, two modalities of breast reconstruction exist: 1) Implant-based and 2) autologous-based breast reconstruction. Implant-based reconstruction involves using an implant to recreate the absent breast and represents 70% of total breast reconstruction procedures (Albornoz C R et al. *Plast Reconstr Surg.* 2013. doi:10.1097/PRS.0b013e3182729cde). Autologous-based reconstruction involves the use of the patient's tissue to reconstruct their breast utilizing microsurgical techniques; this modality represents the remaining 30% and it is considered the gold standard in breast reconstruction, due to more aesthetic results (Hu E S et al. *Plast Reconstr Surg.* 2009. doi: 10.1097/PRS.0b013e3181ab10b2). Patient satisfaction with the reconstruction is of the utmost importance to the mental health and wellbeing of breast cancer survivors after mastectomy. A focus on improving this process will improve the quality of life of many patients.

Autologous breast reconstruction has evolved dramatically; initially, it was intended to only recreate an absent breast. Later, the surgical technique was refined to provide a more aesthetic and natural appearance by improving the mastectomy techniques to utilize the patient's skin envelope and nipple-areola complex to have a more natural result; these improvements resulted in significantly increased patient satisfaction and improved quality of life. Currently, with the advent of more precise microsurgical techniques, some functionality is given to the reconstructed breast by including nerves to provide sensation to the skin and nipple-areola complex, improving the patient's quality of life (Uroskie T W et al. *Semin Plast Surg.* 2004. doi:10.1055/s-2004-829040). These techniques aim to restore breast cancer survivors physically to as close a state as possible to what they enjoyed prior to breast cancer and the lifesaving, but difficult, treatment.

Another important development in autologous breast reconstruction is the utilization of the patients' fat tissue to manage volume, shape and contour deformities. Fat is an appealing filler material that is biocompatible, abundantly available, and can easily be harvested and processed. Although the feasibility of using fat alone as the primary method of reconstruction has been previously reported (Khouri R K et al. *Plast Reconstr Surg.* 2015. doi:10.1097/PRS.0000000000001039; Ho Quoc C et al. *Ann Chir Plast Esthet.* 2016. doi:10.1016/j.anplas.2015.06.010), disadvantages of this technique are the number of sessions needed to achieve symmetry and desired volume, and the high rates of fat necrosis when an excessive amount of fat is transferred into a poorly vascularized pocket, limiting their use (Gabriel A et al. *Gland Surg.* 2015. doi:10.3978/j.issn.2227-684X.2015.04.18). After a series of invasive, painful, and repeated medical interventions to save the lives of breast cancer patients and get them into remission, patients are uninterested in, and often traumatized by, repeated need for medical contact. Thus, it became important to create a method of reconstructing post-mastectomy breast tissue using autologous fat in a single surgical procedure. Herein, a method of using 3D printing is proposed to overcome these challenges.

3D printing. If a network of blood vessels could be 3D printed and surgically connected to the patient vasculature, surgeons could ensure the fat transplant is adequately vascularized, ensuring the best possible outcome for patients. 3D printing technology employing stereolithography can generate exceptionally complex and scalable vascular networks that can engraft in vivo and support the function of embedded parenchymal cells (Grigoryan B et al. *Science* (80-). 2019. doi:10.1126/science.aav9750). Stereolithographic 3D printing uses a photoactive water-based and protein-containing solution that can be crosslinked into a hydrogel through photopolymerization, with a pixel resolution down to 10 μm to construct vessel structures as small as 300 μm in diameter, precisely the target range for this work.

This research also demonstrated that two, non-intersecting vessel systems could be created (FIG. 1) (Grigoryan B et al. *Science* (80-). 2019. doi:10.1126/science.aav9750). The conformation of these vessels can be varied, providing an inter-vessel distance of 300 μm, which is a distance suitable for a vascular network to provide nutrients and oxygen to a payload fat transplant injected into the secondary network. This procedure can be optimized to create multiple fluidic vessels in a way that more closely mimics the architecture of human tissue and thereby uniquely provides a route towards the generation of a vascularized autologous fat implant of arbitrary size and shape to meet the patient's needs.

For this project, the creation of a 3D printed, dual vessel construct, termed the Neobreast, is proposed. The first channel will be connected into the vasculature (described in detail in the research strategy) allowing blood flow through the Neobreast. The second channel will be significantly larger and filled with transplanted fat cells. This will ensure that the fat surround is kept within a specific distance of the artificial vasculature, ensuring blood and oxygen supplies to the transplanted tissues. Prior data suggests that the hydrogel framework is bio-stable for up to eight weeks, allowing time for vascularization by the host system.

Herein, the augmentation of a therapeutic Neobreast with embedded NanoVax in the bulk of the hydrogel is further proposed, to construct a dual-use implant leading to a breakthrough in patient quality of life and disease remission. This design will effectively prevent breast cancer recurrence and metastases while allowing breast cancer survivors to return to their lives soon after mastectomy.

Overarching Challenges. The Neobreast addresses two primary challenges in breast cancer therapy by: 1) significantly reduce the mortality associated with metastatic, recurring breast cancer, and 2) create an immunotherapy-based treatment with greater efficacy and reduced mortality. The Neobreast will create an immunotherapy that prevents recurring breast cancer administered during the reconstructive process. By incorporating the therapeutic BCNanovax into the gel matrix used to create the vasculature, the need for additional treatments is eliminated, allowing patients to focus on healing and returning to their life before cancer. The Neobreast advances reconstructive technology, improving psychological and quality of life outcomes for breast cancer survivors, while the therapeutic arm prevents further disease.

Hypothesis & Specific Aims. It is hypothesized that a well-vascularized 3D printed bio-structure (Neobreast) will have an adequate environment for adipose tissue to survive and serve as an immune organ to expand the immune response to the nano-vaccine, significantly reducing the rate of breast cancer recurrence and distant metastases.

Aim 1 will demonstrate integration of the Neobreast with host vasculature and improved transplant outcomes in small and large animal models. It is hypothesized that the Neobreast architecture will successfully integrate into the host vasculature, increasing the viability of the transplanted fat cells. In order to test this hypothesis, two sub aims have been devised. Sub-aim 1.1 will test Neobreast configurations to determine the optimal formation for integration into a mouse and rabbit model. Within this aim, the ideal shape of the printed vasculature to consistently integrate into the host will be identified. Microsurgical techniques utilizing custom-designed couplers will ensure consistent surgical implantation. Sub aim 1.2 will test Neobreast configurations to optimize transplanted tissue viability. Within this aim, the ideal distance between the fat channels and vasculature channels to ensure the viability of the fat will be identified. Fat viability will be compared to a non-vascularized transplant of equal volume. During this aim, data will be gathered regarding manufacturing processes and material chemistry.

Aim 2 will demonstrate that the NanoVax is safe and provides significant protection from breast cancer recurrence in a rabbit model of breast cancer. The NanoVax has been tested in multiple mouse models but has not been optimized to a large animal, as is necessary for regulatory approval. It is hypothesized that the NanoVax will provoke a significant response in adaptive immune cells leading to reduced breast cancer tumor recurrence. Testing the NanoVax in rabbits will be composed of two parts. Sub aim 2.1 will establish the immune response of a rabbit model to the DC-Nanovaccine. The immune response will be measured by activation of cytotoxic T cells and infiltration of such cells in the tumor tissue. Sub aim 2.2 will demonstrate that treatment with NanoVax reduces tumor burden in a rabbit model of breast cancer. VX2 tumors will be applied to generate a rabbit model of primary breast cancer. Similar to prior work, a majority of the tumor mass will be surgically resected and tumor re-growth will be measured. The procedure mimics pathology of human breast cancer recurrence.

Aim 3 will demonstrate that the Neobreast with the embedded NanoVax is safe in a large animal model and reduces the risk of breast cancer recurrence and distant metastases. This aim focuses on ensuring that the Neobreast is ready to translate from research facilities into the clinics. A large animal model will be utilized to satisfy regulatory requirements. It is hypothesized that the Neobreast with embedded NanoVax will offer superior protection against breast cancer recurrence in the rabbit model. This will be measured by comparing the NanoVax embedded Neobreast with a standard fat flap injection.

This project can provide a fully optimized Neobreast ready to enter the regulatory process for clinical usage. Collaboration with experts in the regulatory process can ensure that a patient-focused approach is maintained. This project can be the transformative step in using 3D printed vasculature for organ transplants.

Research Strategy

Aim 1 will demonstrate integration of the Neobreast with host vasculature and improved transplant outcomes in small and large animal models. While the capability to create a non-intersecting, dual printed channels that can integrate into host vasculature has been demonstrated, it will be validated that this technology works with a fat-loaded channel in the secondary compartment to validate its efficacy for delivery of oxygen and nutrients using the primary vascular channel to the second fat channel. Different Neobreast vascular network topologies will be screened and optimal architectures will be identified that will successfully integrate into the host vasculature and thereby increase the viability of the transplanted fat cells.

In subaim 1.1 Neobreast configurations will be tested to optimize transplanted tissue viability. Hydrogels will be fabricated by stereolithography and will be assessed for vascular efficiency using perfusion tissue culture and human cells transduced with molecular imaging readouts. Briefly, engineered tissues will be fabricated containing luciferase-expressing (Luc2P) HEK cells at 5-50e6 cells/mL within a bulk 20 wt % PEGDA 6 kDa hydrogel. Luciferin substrate will be perfused and luminescence of the hydrogel will be quantified as a function of vascular architecture over 2 hours. Preliminary data on the effect of cell density in hydrogels, as well as the ability to screen algorithmic vascular topologies for luminescence with this assay have been demonstrated. Importantly, the total vascular volume of the hydrogel will be held constant (50 µL in a 1 mL hydrogel) across all topologies, such that the total luminescence provides a direct comparison between the efficiency across networks. Corresponding experiments will be conducted in gels without cells where wall displacement and fluid velocity will be measured via particle image velocimetry (PIV). To map the diffusive transport, the diffusion of fluorescently labeled dextran from the vascular lumen into the interstitial zone will be quantified.

Subaim 1.2 will test Neobreast configurations to determine the optimal formulation for integration into a mouse and rabbit model. The ideal distance between the fat channels and vascular channels in the 0.3 mm-1 mm range will be identified to ensure the viability of the fat. Based on the nature of fat cells, it is believed that the fat channel will need to be significantly larger than the artificially printed blood vessels; fat channels that are 300 µm, 500 µm, and 1 mm in diameter will be tested. Architectural blueprints for the vascular networks are grown computationally that can maximize surface area of the vasculature while minimizing flow resistance and providing for robust mass transport and thus fat tissue survival (Grigoryan B et al. *Science* (80-). 2019. doi:10.1126/science.aav9750).

These vascular constructs can be implanted by a microvascular surgery team. The surgery will be performed in alignment with all regulatory protocols to ensure the justification for the use of research animals involved and for their safety. Surgical operating procedures are outlined more thoroughly in Aim 3. In order to reduce the needed number of animals for these studies, these aims have been designed to be conducted on the same cohort of rabbits, decreasing the time to the proposed outcomes.

The primary outcomes measured in this aim will be fat viability and vascular integration. Histology studies will be used to image transplanted tissue for necrosis, apoptosis, and vascular invasion. Necrosis will be measured by using antibodies against Heat Shock Protein 90 and Histone H1 Complex. Apoptosis will be assessed by using antibodies against caspase 9 and cytochrome c. The goal of these studies is not to differentiate between apoptosis and necrosis, but to provide a full picture of cell death. To measure neovascularization of the transplanted tissue, immunohistochemistry with *Griffonia simplicifolia* Lectin as described in Liang et al. (Liang X L et al. *Int J Ophthalmol.* 2012. doi:10.3980/j.issn.2222-3959.2012.01.01) and confocal microscopy of dual-labeled lectins as described in Baranski et al. (Baranski J D et al. *Proc Natl Acad Sci USA.* 2013. doi:10.1073/pnas. 1217796110) will be used. Should staining methods produce mixed or unclear results, flow cytometry will be utilized.

Aim 1 can provide a functional model of the neobreast that allows increased viability of transplanted fat cells and that can be vascularized by the host organism (FIG. 3-FIG. 8).

Milestones: Aim 1 will demonstrate an improved construct for breast reconstruction. 1. Demonstrate that the Neobreast will allow for increased viability of transplanted fat cells. 2. Prove that the Neobreast will be vascularized by the host organism.

Impact: These studies will allow for significant improvement of breast reconstruction in mastectomy patients. Because these experiments will be conducted in a large animal model, there will be significant support for immediate translation of this work into clinical studies, keeping in line with the BCRP goals of getting improved treatments to breast cancer patients faster.

Aim 2 will demonstrate that NanoVax is safe and provides significant protection from breast cancer recurrence in a rabbit model of breast cancer. NanoVax has been tested in multiple mouse models, but has not been optimized to a large animal, as is necessary for regulatory approval. It is hypothesized that the NanoVax will provoke a significant response in adaptive immune cells leading to reduction or elimination of breast cancer recurrence. Because the overall focus of this project is to move a therapeutic Neobreast to first-in-human trials, large animal studies are essential.

Sub aim 2.1 Establishing the immune response of a rabbit model to the DC-Nanovaccine. New Zealand great white adult female rabbits with VX2 tumors will be applied in the study. The rabbit VX2 tumor was originally established by Shope papilloma virus (SPV) infection, and has been characterized as easy inoculation, rapid growth, and aggressive metastasis. This model has been widely used to assess anti-tumor activity in translational research. The tumor cells will be inoculated by intra-mammary gland injection.

NanoVax will be prepared by loading a Shope virus-specific antigen peptide into 1 μm×400 nm discoidal PSM particles, as an example in the study design.

To analyze the onset and duration of antigen-specific CD8+ T cell production, VX2 tumor-bearing rabbits (n=3 rabbits/group/time point) will be treated twice intradermally with 1) PBS, 2) control vehicle (NanoVax without antigen peptide), or 3) NanoVax, once the tumors are palpable in the mammary gland fat pads and the second time 7 days later. Rabbits will be sacrificed 1 week, 2 weeks, or 3 weeks after the second vaccination (all 3 groups), and blood and tissue samples will be collected for analysis on anti-tumor immune responses.

| Group Name | Treatment | Time Points | N = 27 |
|---|---|---|---|
| Control | PBS | Week 1 | N = 3 |
| | | Week 2 | N = 3 |
| | | Week 3 | N = 3 |
| Control | Vehicle | Week 1 | N = 3 |
| | | Week 2 | N = 3 |
| | | Week 3 | N = 3 |
| Target | NanoVax | Week 1 | N = 3 |
| | | Week 2 | N = 3 |
| | | Week 3 | N = 3 |

Peripheral blood, spleen, and the tumor tissues will be harvested for SPV antigen specific CD8+ T cell measurement with ELISPOT, following the same procedure as recently reported (Xia X et al. *Cell Rep.* 2015. doi:10.1016/j.celrep.2015.04.009). To measure tumor-infiltrating T cells, the tumor tissue will be minced, digested with collagenase, and single cells will be isolated for analysis. Results from this experiment will reveal the time point when the highest level of antigen-specific CD8+ T cells can be detected. This time point will be adopted in the dosage- and dosing schedule-finding studies described next.

To determine dose-dependent activation of T cells by NanoVax, VX2 tumor-bearing rabbits (n=5 rabbits/group/time point) will be treated twice intradermally with 1) control vehicle (NanoVax without antigen peptide), or 2) increasing dosages of NanoVax. Rabbits will be sacrificed, and blood and tissue samples will be collected for analysis on anti-tumor immune responses.

| Group Name | Treatment | Dosage | N = 18 |
|---|---|---|---|
| Control | Vehicle | Low dosage | N = 3 |
| | | Intermediate dosage | N = 3 |
| | | High dosage | N = 3 |
| Target | NanoVax | Low dosage | N = 3 |
| | | Intermediate dosage | N = 3 |
| | | High dosage | N = 3 |

Results from the above studies will be summarized, and the optimal vaccination dosage for effective tumor treatment will be determined, which will guide the efficacy studies. A total of 67 New Zealand white female rabbits are needed for these sub aim experiments.

Sub aim 2.2 will demonstrate that the NanoVax reduces tumor burden in a rabbit model of breast cancer. To demonstrate that the NanoVax reduces tumor burden in a rabbit model, VX2 tumor-bearing rabbits (n=5 rabbits/group) will be treated twice intradermally with 1) Intraflap PBS, 2) Intraflap vehicle (PSM particles without antigen peptide), 3) NanoVax in flap, or NanoVax on the leg. The first treatment is when the tumor is palpable, and the second time 7 days later. Dosages of the vaccine injection will be guided after performing experiments in sub aim 2.1.

| Group Name | Treatment | n = 15 |
|---|---|---|
| Control | Interflap PBS | N = 5 |
| Control | Vehicle | N = 5 |
| Vaccine in Flap | NanoVax | N = 5 |
| Vaccine in non-flap | NanoVax | N = 5 |

It is hypothesized that the intraflap injection will be more therapeutically effective, reducing the tumor burden of rabbits in this group. It is proposed that sustained release of tumor antigen from the NanoVax particles will enable the neighboring adipocytes to constantly process and present antigen epitopes to both conventional T cells and iNKT cells (invariant natural killer t cells). Activated T cells secrete inflammatory cytokines that will not only 1) activate the adipocytes in a positive feedback loop but also 2) convert adipose tissue-associated macrophages to M1 macrophages, and 3) entice dendritic cells from draining lymph nodes into the newly implanted tissue.

Two weeks after tumor inoculation, rabbits in each group will undergo partial tumor resection (50% of initial tumor size) and reconstruction using an advancement flap, including skin and subcutaneous mammary tissue (including adipocytes). Tumor size and flap viability will be measured and monitored daily for three weeks post-op. A total of 15 New Zealand white female rabbits are needed for this sub-aim experiment.

For the surgical procedure, rabbits will be sedated with Ketamine (40 mg/Kg IM) and Xylazine (7 mg/Kg), general anesthesia will be provided using Isoflurane. Rabbits will be sacrificed with an overdose of halogenated anesthetics after the follow-up period; procedures were designed in conjunction with IACUC guidelines.

Results: The goal of Aim 2 is to demonstrate anti-tumor immune responses from our NanoVax in a rabbit model and optimize dosage and dosing schedule to maximize the efficacy. A similar response in a larger animal model as demonstrated in mice models is expected. Since the NanoVax keeps a sustained release pattern of antigen peptides, it is expected that a high level of antigen specific CD8+ T cell population will be maintained inside the tumor tissue. The dose-escalating study in Aim 2.1 will most likely show a plateau of antigen-specific CD8+ T cells when the amount of antigen peptide reaches a certain level, which will be the working dose for the Aim 2.2 efficacy study.

After demonstrating the vaccine efficacy and optimizing its parameters in a large animal model, two different routes of administration will be analyzed, intradermal and intraflap. Since adipocytes express major histocompatibility complex II (MHC II) and the non-classic MHC protein CD1d, and can serve as antigen-presenting cells to stimulate both the conventional T lymphocytes (CD4+ T cells and CD8+ T cells) and the invariant natural killer T (iNKT) cells, therefore expanding the host immune response it is expected to have a quicker tumor regression response in the group where the NanoVax is injected. This approach will open the door of a new research field, where autologous tissue that is normally used in breast reconstruction technique, could serve as a vehicle of our NanoVax.

Milestones: Aim 2 will demonstrate that the NanoVax is safe and provides significant protection from breast cancer recurrence in a rabbit model of breast cancer. 1. Analysis on activation of CD8+ T cell activation by NanoVax vaccine in vivo. 2. Determination of optimal dosage and dosing schedule for NanoVax in vivo. 3. Evaluation of therapeutic efficacy from NanoVax with two different routes of administration in New Zealand white rabbits.

Aim 3: Demonstrate that the Neobreast with the embedded NanoVax is safe in a large animal model and reduces the risk of breast cancer recurrence and distant metastases. Fat tissue (adipocytes) is an appealing filler material for breast reconstruction because it is biocompatible, abundantly available, and easily harvested for use. The need for vasculature connection limits current methods of transplanting cells; by printing the vasculature, the size of transplanted tissues can be expanded and cellular death can be prevented. Therefore, an adequate environment can be created for transplanted fat tissue to survive and serve as the immune organ to expand the host immune response to NanoVax. As proposed in sub aim 2.2, it is expected to demonstrate that Nano-vaccine will trigger the expansion of E75-specific T cells in an environment full of adipocytes and increase their efficacy in a large animal as we have seen in small animal models.

It is hypothesized that Neobreast comprising 3D printed fat channels, blood vessels, and artificial lymph nodes will be an adequate vehicle to expand host immunity to NanoVax and further improve their efficacy in reducing breast cancer recurrence and distant metastases.

Sub aim 3.1. Establishing the immune response of a rabbit model to the NanoVax embedded in the neobreast. New Zealand great white adult female rabbits with orthotopic VX2 tumors will be utilized in the study. The tumor will be generated by intra-mammary gland inoculation of VX2 cells. As performed in sub aim 2.1, the onset and duration of antigen-specific CD8+ T cell production will be analyzed.

VX2 tumor rabbits (n=3 rabbits/treatment group/time point) will undergo partial tumor resection and defect coverage (reconstruction) in three groups as follow: 1) Advancement flap with i.d NanoVax, 2) Advancement flap with intraflap NanoVax and 3) Microsurgically connected neobreast+NanoVax when the tumors are palpable in the mammary gland fat pads. Mice will be sacrificed 1, 2, or 3 weeks after vaccination.

| Group Name | Treatment | Time Points | N = 27 |
|---|---|---|---|
| Standard-delivery NanoVax | Advancement flap with i.d. NanoVax | Week 1 | N = 3 |
| | | Week 2 | N = 3 |
| | | Week 3 | N = 3 |
| Fat-delivery NanoVax | Advancement flap with intraflap NanoVax | Week 1 | N = 3 |
| | | Week 2 | N = 3 |
| | | Week 3 | N = 3 |
| Therapeutic Neobreast | Microsurgically connected Neobreast + NanoVax | Week 1 | N = 3 |
| | | Week 2 | N = 3 |
| | | Week 3 | N = 3 |

Peripheral blood, spleen, and tumor tissues will be harvested for antigen-specific CD8+ T cell measurement with ELISPOT, as recently reported (Xia X et al. *Cell Rep.* 2015. doi:10.1016/j.celrep.2015.04.009). To measure tumor-infiltrating T cells, the tumor tissue will be minced, digested with collagenase, and single cells will be isolated for analysis. Results from this experiment will be analyzed in two forms. First, by comparing within each treatment group across the time points, the highest level of antigen-specific CD8+ T cells will be identified. Second, a comparison between the three treatment groups will be performed at each time point. A total of 27 female adults New Zealand white rabbits will be needed for this experiment.

Microsurgical connection of Neobreast: The 3D printed developed breast will be connected to the superficial inferior epigastric artery (SIEA). The anatomy was outlined by Giessler et al., where they described the design of the SIEA fascia flap in a rabbit model (Giessler G A et al. *Microsurgery*. 2007. doi:10.1002/micr.20413). A 1-mm Synovis® artery coupler will be used to perform the microsurgical connection between the 3D printed blood vessel and the superficial inferior epigastric artery. This procedure will be performed on a total of 15 rabbits.

Alternative microsurgical connection: If there are potential issues with the microsurgical connection, as an alternative, instead of using the SIEA vessel, the femoral artery could be used as the main vessel where the neobreast will be connected. As demonstrated in a rat model by Zhang et al., previously 3D printed blood vessels models (AngioChips) can be anastomosed to the femoral artery using an artery-to-artery or an artery-to-vein anastomosis (FIG. 9) (Zhang B et al. *Nat Mater.* 2016. doi:10.1038/nmat4570).

Sub aim 3.2. Demonstrate that the Neobreast+NanoVax reduces tumor burden in a rabbit model of breast cancer. VX2 tumor rabbits (n=5 rabbits/group/time point) will undergo partial tumor resection and defect coverage (reconstruction) in three groups as follow: 1) Microsurgically connected neobreast without NanoVax (Control group) 2) Microsurgically connected neobreast+NanoVax, and 3) Advancement flap with intraflap NanoVax injection. In each group, tumor size and flap viability will be measured and monitored daily for three weeks post-op. For the surgical procedure, rabbits will be sedated with Ketamine (40 mg/Kg IM) and Xylazine (7 mg/Kg), general anesthesia will be provided using Isoflurane. Rabbits will be sacrificed with an overdose of halogenated anesthetics after the follow-up period.

Results: The goal for Aim 3 is to demonstrate the efficacy of the 3D printed neobreast with the DC-Nanovaccine embedded in the hydrogel. Since the fat tissue should improve and expand the host immune response to the DC-Nanovaccine, it is expected that a 3D printed biostructure with all the necessary components for an adequate environment for adipocytes to survive will serve as a vehicle to improve the efficacy of the DC-Nanovaccine and decreasing breast cancer recurrence in a large animal model. Specifically, for sub aim 3.1 a high level of antigen-specific CD8+ T cell population is expected in group #3 (Microsurgically connected neobreast+DC-Nanovaccine). After demonstrating the vaccine efficacy and optimizing its parameters in a large animal model, two different routes of administration will be analyzed, intradermal and intraflap. Since adipocytes express major histocompatibility complex II (MHC II) and the non-classic MHC protein CD1d, and can serve as antigen-presenting cells to stimulate both the conventional T lymphocytes (CD4+ T cells and CD8+ T cells) and the invariant natural killer T (iNKT) cells, therefore expanding the host immune response is expected to have a quicker tumor regression response in the group where the NanoVax is injected while the therapeutic Neobreast group will have less tumor growth. This approach will open the door of a new research field, where autologous tissue that is normally used in breast reconstruction technique, could serve as a vehicle of our DC-nanovaccine.

Milestones: Demonstrate that the Neobreast with the embedded DC-Nanovaccine is safe in a large animal model and reduces the risk of breast cancer recurrence and distant metastases. 1. Analysis of activation of CD8+ T cell activation by Neobreast+NanoVax in vivo. 2. Evaluation of therapeutic efficacy of Neobreast+NanoVax in New Zealand white rabbits.

Statistical Plan. Mean and standard deviation (SD) will be used to describe normally distributed data. Median and interquartile range (IQR) will be used to describe non-normally distributed data. For this proposal, either two or three study groups will be compared at different study points. A comparison of normally distributed continuous variables will be performed using the student t-test; a comparison of two non-normally distributed data will be performed using Mann-Whitney or Wilcoxon rank-sum test. When comparing continuous variables in more than two groups, one-way ANOVA and Kruskal-Wallis tests will be used for normally and non-normally distributed data, respectively. Regarding categorical data, Chi-square and Fisher's exact test will be used for either comparison between two or three groups. When comparing categorical variables of more than two groups, post-hoc analyses will be performed. If necessary, binary regression analysis will be performed when analyzing categorial binary outcome variables. A significance level is defined at p-value<0.05. SPSS software (Version 25.0. Armonk, N.Y., IBM Corp.) will be used for all statistical analyses.

Significance. Breast cancer is a multifaceted disease, the treatment of which goes far beyond the initial declaration of "Cancer Free." 40% of breast cancer patients have a mastectomy or lumpectomy as part of their cancer treatment. These women often experience significant anxiety and depression regarding their mastectomy (Wong C A et al. *Cancer Nurs.* 1992. doi:10.1097/00002820-199210000-00006; Garofalo J P et al. *Cancer Nurs.* 2009. doi:10.1097/NCC.0b013e31819f1aab). The mental distress is long-lasting, with persistent levels of anxiety and stress fifteen months post-mastectomy (Kyranou M et al. *Cancer Nurs.* 2014. doi:10.1097/NCC.0000000000000131; Lebel S et al. *J Cancer Surviv.* 2009. doi:10.1007/s11764-009-0082-5), and significantly compromises the quality of life for survivors (Taylor T R et al. *Int J Behav Med.* 2012. doi:10.1007/s12529-011-9183-4). 77% of breast cancer patients will be treated for depression within two years of their cancer-free diagnosis (Ashbury F D et al. *J Pain Symptom Manage.* 1998. doi:10.1016/S0885-3924(98)00102-X). Anxiety and depression after mastectomy can be partially attributed to a significant fear of cancer reoccurrence, which can be severe enough to drive survivors to oncologists and emergency rooms, sure that their cancer has reoccurred. To improve quality of life, it is necessary to create a systematic treatment that will prevent reoccurrence and reduce mortality without requiring additional office visits and procedures, allowing cancer survivors to return to a healthy life. Incorporating the DC-Nanovax into the Neobreast will serve precisely this purpose. The NanoVax will provide superior protection against reoccurrence, giving patients the peace of mind they so desperately need.

Patients who undergo a mastectomy show increased rates of anxiety and depression compared to breast cancer survivors who did not undergo mastectomy, attributed to concerns about body image as well as "psychosocial and sexual conflicts" around the loss of one or both breasts (Farooqi Y N. *Illn Cris Loss.* 2005. doi:10.1177/1054137305013003306). Breast reconstruction can reduce anxiety and depression in these patients, with immediate reconstruction having significant benefits even when compared to delayed reconstruction (Heimes A S et al. *Breast Care.* 2017. doi:10.1159/000485234). However, even immediate reconstruction does not eliminate the risk of anxiety and depression (Montebarocci O et al. *Psychol Rep.* 2007. doi:10.2466/PR0.101.1.100-106). Reconstruction, as it stands, is an imperfect science. Breast symmetry is a primary concern, but implants are limited in their ability to achieve a perfectly symmetrical appearance, thus current implant technology is undesirable (Montebarocci O et al. *Psychol Rep.* 2007. doi:10.2466/PR0.101.1.100-106; Bellino S et al. *Plast Reconstr Surg.* 2011. doi:10.1097/PRS.0b013e3181f956c0; Serletti J M et al. *Plastic Surgery Complete: The Clinical Masters of PRS—Breast Reconstruction.;* 2015. doi:10.1097/PRS.0b013e318213a2e6; Nahabedian M Y. *Plast Reconstr Surg.* 2005. doi:10.1097/01.PRS.0000146679.82558.5E). Therefore, new methods of reconstruction are necessary. The Neobreast is not limited to several fabricated shapes and sizes intended to fit all women. Unlike implants, reconstruction utilizing autologous tissue results in a reconstructed breast that follows changes in body dynamics, like weight gain, and patients have higher satisfaction rates. The Neobreast significantly improves upon autologous grafting for reconstruction by providing a vascularized scaffold for the fat, improving the efficacy of the transport. Vascularizing the tissue provides a significant advantage and expands access to this method of reconstruction. Cancer survivors do not stop being patients as soon as they are cancer-free; reconstructive care improves the quality of life and reduces symptoms of mental distress in cancer survivors. This aspect of care is continually underserved, and the Neobreast creates significant benefits in this space.

Beyond cancer reconstruction, this technology has potential in many spaces. The Neobreast will prove a technology of pre-vascularizing a transplanted organ, in this case, fat. Success with the Neobreast will provide an avenue of research into similar research studies implanting other organs and tissues.

The Neobreast is an approach that will move breast cancer therapy forward. The Neobreast addresses significant challenges by providing a less invasive, less toxic treatment that will significantly impact breast cancer survival and breast cancer reoccurrence and metastasis. Reducing the risk of reoccurrences will reduce anxiety after breast cancer, improving quality of life. This, in conjunction with the clear benefits of improving reconstructive therapy, make the Neobreast, a leap forward in the care of breast cancer patients.

Example 6

Breast cancer is the most common malignancy in women worldwide. Due to earlier diagnosis and improvement of treatments, a rising number of women live longer and therefore are at risk of developing tumor recurrence, which is associated with poor outcomes and an increase in distant metastases (Siegel R L. Cancer Statitcs. *CA Cancer J Clin.* 2019). The treatment of breast cancer recurrence and metastases usually involves chemo and radiotherapy, however, these modalities have their limitations. Therefore, new treatment modalities are required.

Overarching challenges will be addressed by this work: (1) revolutionize treatment regimens by replacing them with ones that are more effective, less toxic and impact survival and (2) eliminate the mortality associated with metastatic breast cancer. The Neobreast will improve survival in recurrent breast cancer with fewer toxic treatments.

It is hypothesized that a pre-vascularized 3D printed bio-structure (Neobreast) will have a better environment for adipose tissue to survive and serve as an immune organ to expand the immune response to a DC-Nanovaccine, significantly reducing the rate of breast cancer recurrence.

Specific aims: Aim 1. Demonstrate integration of the Neobreast with host vasculature and improved transplant outcomes in small and large animal models. Aim 2. Demonstrate that the DC-Nanovaccine is safe and provides significant protection from breast cancer recurrence in a rabbit model of breast cancer. Aim 3. Demonstrate that the Neobreast with the embedded DC-Nanovaccine is safe in a large animal model and reduces the risk of breast cancer recurrence and distant metastases.

Summary of Research Plan:

Aim 1 will demonstrate integration of the Neobreast with host vasculature and improved transplant outcomes in small and large animal models. Subaim 1.1 will test Neobreast configurations to optimize transplanted tissue viability. Subaim 1.2 will test Neobreast configurations to determine the optimal formulation for integration into a mouse and rabbit model.

Aim 2 will demonstrate that NanoVax is safe and provides significant protection from breast cancer recurrence in a rabbit model of breast cancer. Subaim 2.1 will establish the immune response of a rabbit model to the DC-Nanovaccine Sub aim 2.2 will demonstrate that the NanoVax reduces tumor burden in a rabbit model of breast cancer.

Aim 3 will demonstrate that the Neobreast with the embedded NanoVax is safe in a large animal model and reduces the risk of breast cancer recurrence and distant metastases. Subaim 3.1 will establish the immune response of a rabbit model to the NanoVax embedded in the neobreast. Subaim 3.2 will demonstrate that the Neobreast+NanoVax reduces tumor burden in a rabbit model of breast cancer.

Study design: This work involves a three-phase study. During phase one, a 3D-printed biostructure (Neobreast) will be designed and developed based on existing work developing 3D printed vasculature. This structure will include blood vessels, fat channels, and lymphatic channels with the ability to house adipocytes and DC-Nanovaccine. After this phase, a functional prototype of a Neobreast will be obtained that will serve as a vehicle to deliver therapeutic agents. Phase two of this study will be to investigate and establish the immune response of a New Zealand Rabbit model to the DC-Nanovaccine and to demonstrate that the DC-Nanovaccine reduces tumor burden in a rabbit model. Lastly, in phase three, the information gleaned in phases one and two will be incorporated to microsurgically anastomose the developed bio-structure in a rabbit breast cancer model to determine if the Neobreast+the developed DC-vaccine reduces tumor burden. Phase 3 will be the building block for proposing clinical studies moving this work into first-in-human studies.

Impact: This proposal has a three-fold impact. First, by developing an innovative vehicle for breast cancer immunotherapy with sustainable immune response by the host, it is expected to decrease breast cancer recurrence rates in patients who underwent a mastectomy, therefore, increasing long-term survival in this population. Breast cancer survivors commonly experience anxiety regarding the risk of reoccurrence; this anxiety can be so intense that it manifests physically, driving patients to emergency rooms, believing their cancer has reoccurred (Breastcancer.org. US Breast Cancer Statistics. US Breast Cancer Statistics. https://www-.breastcancer.org/symptoms/understand_bc/statistics. Published 2019. Accessed Oct. 3, 2019). The Neo-breast would reduce patient anxiety, improving Quality of Life without additional treatments or doctor visits. Second, the Neo-breast will be the first time a new modality of breast reconstruction would have preventive/therapeutic indications in postmastectomy patients, reinforcing the fact that breast reconstruction is a continuum of breast cancer treatment. Third, with the development of a 3D printed biological structure with therapeutic features, a new door is opened for potential future transplantations, and drug delivery approached for a variety of organs such as liver, kidney, and lungs, among others.

Example 7

Breast cancer is the most common cancer in women worldwide; approximately 300,000 new breast cancer cases were diagnosed in 2019 alone. Advances in research and medical science have led to early diagnosis and treatments, improving survival rates. Unfortunately, increased survival rates have also driven the number of women who are at risk for breast cancer recurrence up significantly. Breast cancer recurrence is associated with increased metastases and poor survival; this is a significant cause of death due to breast cancer that needs focused attention.

Breast cancer survivors, aware of the risk of recurrence, often experience significant anxiety that reduces their quality of life. With this in mind, an immunotherapy, a vaccine, against recurrent breast cancer has been developed. This vaccine, delivered to the tumor site soon after treatment of the original cancer, could prevent a recurrence. This long-term treatment would reduce anxiety in breast cancer survivors, improving their quality of life. It would also prevent significantly more deadly recurrent and metastatic breast cancer. There is strong evidence in animal models that this vaccine can effectively prevent the growth and spread of cancerous tumors.

To further address quality of life concerns for breast cancer patients, this technology is partnered with research on breast reconstruction. While a majority of breast cancer patients who have a mastectomy seek reconstruction, there are significant concerns that current reconstructive therapy is not meeting the needs of survivors. Current technology allows for a breast implant to be used for reconstruction, which often results in poor symmetry, with patients unhappy with the final result. Alternatively, reconstruction can be done with fat transplanted from the patient's abdomen. Fat is a significantly better reconstructive medium because it integrates into the patient, changing as her body changes. For example, cancer patients often experience changes in weight as they recover from their treatment; implants do not change with the patient, while transplanted fat changes. However, large transplants are not possible; without the vasculature to feed the cells, they will die soon after transplant. Instead, surgeons must transplant small amounts of fat over time to achieve a final appearance pleasing to the patient. Frequently returning for surgery can be distressing to cancer patients who want to get back to the business of building their lives.

Thus, a technique of 3D printing artificial, biocompatible vasculature is developed. This vasculature can be surrounded with transplanted fat and implanted during the reconstructive process. Microvasculature surgery can be used to reconnect these artificial veins, allowing much larger fat transplants. With this method, a patient could have a single surgery. By embedding a vaccine into the 3D printed vasculature, uptake and immune system response can be improved, providing better protection than other delivery routes. Patients will have a single reconstructive surgery directly after their mastectomy and leave with an appearance they are satisfied with and the knowledge that they are protected from cancer recurrence.

This project can improve the lives of breast cancer survivors around the world. A reconstructive technology is described that can improve patient satisfaction with their appearance after mastectomy while protecting them from cancer, letting patients stop worrying about cancer, and focus on living.

By the end of this project, a 3D printed vasculature will be developed that can support transplanted fat, producing a viable, vascularized organ: the Neobreast. The impact of this work is threefold. First, by developing a vehicle for breast cancer immunotherapy with sustainable immune response by the host, the rates of breast cancer recurrence and distant metastases in patients that underwent a mastectomy are expected to decrease, therefore, increasing long-term survival in this population. Breast cancer survivors commonly experience anxiety regarding the risk of reoccurrence; this anxiety can be so intense that it manifests physically, driving patients to emergency rooms, believing their cancer has reoccurred. The Neobreast would reduce patient anxiety, improving Quality of Life without additional treatments or doctor visits. Second, the Neobreast will be the first time a new modality of breast reconstruction would have preventive/therapeutic indications in postmastectomy patients, reinforcing the fact that breast reconstruction is a continuum of breast cancer treatment. Third, with the development of a functional 3D printed biological structure with therapeutic features, a new door is opened for potential future transplantations and drug delivery approached for a variety of organs such as liver, kidney, and lungs, among others.

Other advantages which are obvious and which are inherent to the invention will be evident to one skilled in the art. It will be understood that certain features and sub-combinations are of utility and may be employed without reference to other features and sub-combinations. This is contemplated by and is within the scope of the claims. Since many possible embodiments may be made of the invention without departing from the scope thereof, it is to be understood that all matter herein set forth or shown in the accompanying drawings is to be interpreted as illustrative and not in a limiting sense.

The methods of the appended claims are not limited in scope by the specific methods described herein, which are intended as illustrations of a few aspects of the claims and any methods that are functionally equivalent are intended to fall within the scope of the claims. Various modifications of the methods in addition to those shown and described herein are intended to fall within the scope of the appended claims. Further, while only certain representative method steps disclosed herein are specifically described, other combinations of the method steps also are intended to fall within the scope of the appended claims, even if not specifically recited. Thus, a combination of steps, elements, components, or constituents may be explicitly mentioned herein or less, however, other combinations of steps, elements, components, and constituents are included, even though not explicitly stated.

What is claimed is:

1. A device comprising:
   a continuous hydrogel matrix;
   a first chamber in the hydrogel matrix; and
   a second chamber in the hydrogel matrix;
   wherein the first chamber and the second chamber are each independently perfusable;
   wherein the first chamber is fluidly independent from the second chamber;
   wherein the first chamber is configured to be at least partially filled with adipose tissue;
   wherein the second chamber is configured to be at least partially filled with an oxygenated fluid;
   wherein the first chamber is defined by a first border;
   wherein the second chamber is defined by a second border; and
   wherein the first chamber and the second chamber are spaced apart from each other by an average distance of from 50 micrometers (microns, μm) to 800 μm as measured from the first border to the second border.

2. The device of claim 1, wherein the first chamber and the second chamber are entangled.

3. The device of claim 1, wherein the first chamber and the second chamber are spaced apart from each other by an average distance of from 200 μm to 400 μm.

4. The device of claim 1, wherein the first chamber has an average characteristic dimension of from 150 μm to 10 millimeters (mm).

5. The device of claim 1, wherein the first chamber further comprises an inlet configured to receive the adipose tissue.

6. The device of claim 1, wherein the second chamber has an average characteristic dimension of from 5 μm to 500 μm.

7. The device of claim 1, wherein the second chamber has a longitudinal axis, an inlet, and an outlet axially spaced apart from the inlet, wherein the inlet is configured to receive the oxygenated fluid and the outlet is configured to discharge the oxygenated fluid.

8. The device of claim 7, wherein the oxygenated fluid comprises blood and the inlet and the outlet of the second chamber are each independently configured to be connected to a blood vessel.

9. The device of claim 1, wherein the second chamber is lined with a plurality of endothelial cells.

10. The device of claim 1, wherein the device further comprises a third chamber in the hydrogel matrix, wherein the third chamber is perfusable and fluidly independent from the first chamber and the second chamber.

11. The device of claim 10, wherein the third chamber is configured to be at least partially filled with a lymphatic fluid.

12. The device of claim 11, wherein:
   the third chamber further comprises a port configured to allow for the flow of the lymphatic fluid into and out of the third chamber; or
   wherein the third chamber has a longitudinal axis, an inlet, and an outlet axially spaced apart from the inlet, wherein the inlet is configured to receive the lymphatic fluid and the outlet is configured to discharge the lymphatic fluid.

13. The device of claim 1, wherein the device further comprises a therapeutic agent dispersed within the hydrogel matrix.

14. The device of claim 1, wherein the first chamber is at least partially filled with adipose tissue.

15. The device of claim 1, wherein the device is implantable in a subject.

16. The device of claim 15, wherein the device is anatomically designed for the subject.

17. The device of claim 15, wherein the hydrogel matrix is configured to be stable for an amount of time of from 6 weeks to 12 weeks after the device is implanted in the subject.

18. The device of claim 1, wherein the device is produced by additive manufacturing.

19. A device comprising multiple joined subunits, wherein each subunit independently comprises:
a continuous hydrogel matrix; and
one or more chambers in the continuous hydrogel matrix;
wherein each of the one or more chambers in each subunit is fluidly independent from one another;
wherein, when multiple subunits are joined together, the device comprises:
a continuous hydrogel matrix;
a first chamber in the hydrogel matrix; and
a second chamber in the hydrogel matrix;
wherein the first chamber and the second chamber are each independently perfusable;
wherein the first chamber is fluidly independent from the second chamber;
wherein the first chamber is configured to be at least partially filled with adipose tissue;
wherein the second chamber is configured to be at least partially filled with an oxygenated fluid;
wherein the first chamber is defined by a first border;
wherein the second chamber is defined by a second border; and
wherein the first chamber and the second chamber are spaced apart from each other by an average distance of from 50 micrometers (microns, μm) to 800 μm as measured from the first border to the second border.

20. The device of claim 19, wherein the first chamber and the second chamber are entangled.

21. The device of claim 19, wherein the first chamber and the second chamber are spaced apart from each other by an average distance of from 200 μm to 400 μm.

22. The device of claim 19, wherein the device further comprises a third chamber in the hydrogel matrix, wherein the third chamber is perfusable and fluidly independent from the first chamber and the second chamber.

23. The device of claim 22, wherein the third chamber is configured to be at least partially filled with a lymphatic fluid.

24. The device of claim 23, wherein:
the third chamber further comprises a port configured to allow for the flow of the lymphatic fluid into and out of the third chamber; or
the third chamber has a longitudinal axis, an inlet, and an outlet axially spaced apart from the inlet, wherein the inlet is configured to receive the lymphatic fluid and the outlet is configured to discharge the lymphatic fluid.

25. The device of claim 19, wherein the device further comprises a therapeutic agent dispersed within the hydrogel matrix.

26. The device of claim 19, wherein the first chamber is at least partially filled with adipose tissue.

27. The device of claim 19, wherein the device is implantable in a subject.

28. The device of claim 27, wherein the device is anatomically designed for the subject.

29. The device of claim 28, wherein the hydrogel matrix is configured to be stable for an amount of time of from 6 weeks to 12 weeks after the device is implanted in the subject.

30. The device of claim 19, wherein the device is produced by additive manufacturing.

* * * * *